United States Patent [19]

Wilhelm et al.

[11] Patent Number: 5,455,252
[45] Date of Patent: Oct. 3, 1995

[54] OPTIONALLY SUBSTITUTED 6,8-QUINOLINES

[75] Inventors: Robert S. Wilhelm, Mountain View; Paul R. Fatheree, San Francisco; Ronnie L. Chin, Mountain View, all of Calif.

[73] Assignee: Syntex (U.S.A.) Inc., Palo Alto, Calif.

[21] Appl. No.: 40,731

[22] Filed: Mar. 31, 1993

[51] Int. Cl.$^6$ .................. A61K 31/47; C07D 215/04; C07D 215/12
[52] U.S. Cl. .................. 514/311; 514/314; 514/826; 546/107; 546/173
[58] Field of Search .................. 546/173, 168, 546/167; 514/311, 314, 826

[56] References Cited

U.S. PATENT DOCUMENTS 4,563,460  1/1986  Kuhla et al. .................. 514/260

FOREIGN PATENT DOCUMENTS 2028314      4/1991   Canada .................. C07D 215/14
0184437A2    6/1986   European Pat. Off. .......... C12Q 1/26
03040632A2   2/1989   European Pat. Off. ....... C07D 215/18

OTHER PUBLICATIONS

Price, et al., "J. Amer. Chem. Soc.", vol. 68, No. 12, pp. 2589–2592, 1946.
Ollis, W. D. et al., "Heterocyclic Mesomeric Betaines. Part 2. Synthesis of a Hetero Derivative of the Benzo[b]phenalenide Anion", *J. Chem. Soc. Perkin Trans. I*, (1989), No. 5, pp. 953–956.
Hassanaly, P. et al., "Homolytic Aromatic Substitution by Heterocyclic Free Radicals. Reaction of 3–Quinolyl and 8–Quinolyl Radicals with Aromatic Compounds", *J. Heterocyclic Chem.*, Aug. 1975, vol. 12, pp. 703–704.
Wommack, J. B. et al., "The Synthesis of Quinoline– and Isoquinolinecarboxaldehydes", *J. Heterocyclic. Chem.*, Apr. 1969, vol. 6, No. 2, pp. 243–245.
Hönel, M. et al., "Selectivity in the Hydrogenation of 6– and 8–Substituted–quinolines", *J. Chem. Soc. Perkin Trans. I*, (1980), No. 9, pp. 1933–1939.

Primary Examiner—C. Warren Ivy
Assistant Examiner—Raymond Covington
Attorney, Agent, or Firm—Rohan Peries; Brian Lewis

[57] ABSTRACT

A compound of the formula

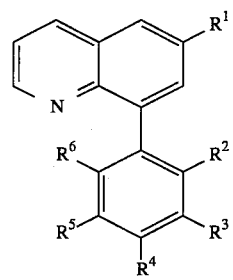

Formula I wherein:

$R^1$ is independently selected from hydrogen, lower-alkyl, cycloalkyl, cycloalkyl lower-alkyl, lower-alkoxy, formyl, (lower-alkyl)-hydroxylmethyl, aryl, benzyl, arylmethyl, pyridylmethyl, where aryl, benzyl, arylmethyl and pyridylmethyl are unsubstituted or independently mono, di or tri substituted with hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl; and $R^2$, $R^3$, $R^4$, $R^5$ and $R^6$ are as set forth in the specification.

21 Claims, No Drawings

OPTIONALLY SUBSTITUTED 6,8-QUINOLINES

BACKGROUND OF THE INVENTION

1. Field of the Invention

This invention relates to optionally 6,8-substituted quinolines useful as anti-inflammatory agents, immunosuppressive agents, anti-allograft rejection agents, anti-graft-vs-host disease agents, anti-allergic agents (e.g., asthma, rhinitis and atopic dermatitis), bronchiodilation agents, anti-autoimmune agents or analgetic agents, to their precursors, to their preparation and to pharmaceutical compositions using the compounds of the invention.

2. Background Information

Cyclic 3',5'-adenosine monophosphate (cAMP) modulates a variety of cellular and physiologic functions in mammals, such as, cell division, endocrine function, and the immune response. The level of cAMP is controlled by a class of enzymes called phosphodiesterases, which enzymatically deactivate cAMP. There are five general types of phosphodiesterases, which are categorized according to their function and the type of cell from which they are isolated. For instance, high-affinity phosphodiesterase (PDE III) is isolated from human platelet cells and modulates platelet aggregation. Another type of phosphodiesterase (PDE IV) is found in various tissues but is the predominant form in human leukocytes; this enzyme modulates leukocyte activation and function associated with the immune response and inflammation. Both of these phosphodiesterases implement their control by modulating the cellular level of cAMP in their respective cells. Thus, inhibition of phosphodiesterases provides a method of modulating any cellular and bodily function that is controlled by cAMP.

Compounds that are nonspecific phosphodiesterase inhibitors are known, i.e., these compounds inhibit all or multiple types of phosphodiesterases. [See, Beavo, J. A. and D. H. Reifsyder, Trends in Pharm. Science, 11:150–155 (1990); and Nicholson, C. D., R. A. J. Challiss and M. Shahid, Trends in Pharm. Science, 12:19–27 (1991).] Since cAMP is involved in so many functions throughout the body, a nonspecific phosphodiesterase inhibitor has the potential to alter all of the functions modulated by cAMP, thus nonspecific phosphodiesterase inhibitors are of limited value because of numerous side-effects.

It has been surprisingly discovered that certain optionally substituted 6,8-quinolines are potent selective inhibitors of Phosphodiesterase Type IV (PDE IV). These compounds are well suited for use as a treatment for any disorder in which PDE IV function plays a role, such as where leukocyte activation or function is involved. In particular, these compounds are especially well suited for use as anti-inflammatory agents, immunosuppressive agents, anti-allograft rejection agents, anti-graft-vs-host disease agents, anti-allergic agents (e.g., asthma, rhinitis and atopic dermatitis), bronchiodilation agents, anti-autoimmune disease agents or analgetic agents.

SUMMARY OF THE INVENTION

One aspect of the present invention relates to optionally substituted 6,8-quinolines, i.e., a compound of Formula I:

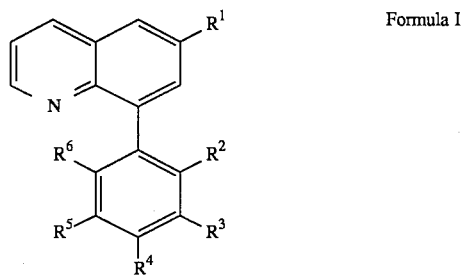

Formula I wherein:

$R^1$ is independently selected from hydrogen, lower-alkyl, cycloalkyl, cycloalkyl lower-alkyl, lower-alkoxy, formyl, (lower-alkyl)-hydroxylmethyl, aryl, benzyl, arylmethyl, pyridylmethyl, where aryl, benzyl, arylmethyl and pyridylmethyl are independently mono, di or tri substituted with hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl; and $R^2$, $R^3$, $R^4$, $R^5$ and $R^6$ are independently selected from hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl or a pharmaceutically acceptable ester, ether, N-oxide or salt thereof.

Preferred aspects of $R^1$ are pyridylmethyl, benzyl, cycloalkylmethyl or lower alkyl.

Preferred aspects of $R^3$ and/or $R^4$ are electron-withdrawing groups.

In another aspect, the invention relates to a pharmaceutical composition containing a therapeutically effective amount of a compound of Formula I or a pharmaceutically acceptable ester, ether, N-oxide or salt thereof admixed with at least one pharmaceutically acceptable excipient.

In still another aspect, the invention relates to a method of use as an anti-inflammatory agent, immunosuppressive agent, anti-allograft rejection agent, anti-graft-vs-host disease agent, anti-allergic agent (e.g., asthma, rhinitis and atopic dermatitis), bronchiodilation agents, anti-autoimmune disease agent or analgetic agent, by administering to a mammal in need of such treatment a therapeutically effective amount of a compound of Formula I or a pharmaceutically acceptable ester, ether, N-oxide or salt thereof.

Yet another aspect of the invention relates to the treatment of the above conditions or diseases by the selective inhibition of PDE IV.

In another aspect, this invention provides compositions useful in the treatment of inflammatory, allograft rejection, graft-vs-host disease, allergy, autoimmune or analgetic conditions or diseases in mammals comprising a therapeutically effective amount of a compound of Formula I or a pharmaceutically acceptable ester, ether, N-oxide or salt as described above and a pharmaceutically acceptable excipient.

DETAILED DESCRIPTION

Definitions and General Parameters

The following definitions are set forth to illustrate and define the meaning and scope of the various terms used to describe the invention herein.

The term "alkyl" refers to a branched or straight chain monovalent saturated aliphatic hydrocarbon radical of one to twenty carbon atoms.

The term "lower-alkyl" refers to a branched or straight chain monovalent alkyl radical of one to four carbon atoms. This term is further exemplified by such radicals as methyl, ethyl, n-propyl, isopropyl, i-butyl, n-butyl and t-butyl.

The term "cycloalkyl" refers to a monovalent carbocyclic radical of one to six carbon atoms, which can optionally be mono-, di-, or tri-substituted, independently, with hydrogen, hydroxyl, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl.

The term "cycloalkyl lower-alkyl" refers to a cycloalkyl group attached to a parent structure via a lower-alkyl group. For example, cyclopropylmethyl, cyclopentylethyl, cyclopentylpropyl, or cyclopentylmethyl.

The term "lower alkoxy" refers to the group —O—R' where R' is lower alkyl.

The term "methylene" refers to the group —CH₂—.

The term "carbonyl" refers to the group —C(O)—.

The term "hydroxycarbonyl" refers to the group —C(O)OH.

The term "lower-alkoxycarbonyl" refers to the group —C(O)OR' where R' is lower-alkyl.

The term "acyl" refers to the group —C(O)—R', where R' is lower-alkyl, e.g., methylcarbonyl and ethylcarbonyl.

The term "carbamoyl" refers to the group —C(O)NR'R where R and R' are independently hydrogen or lower-alkyl, e.g., where R is hydrogen and R' is lower-alkyl the group is lower-alkylcarbamoyl, where R and R' are lower-alkyl the group is di-lower-alkylcarbamoyl.

The term "halo" refers to fluoro, bromo, chloro and iodo.

The term "lower-alkylthio" refers to the group R—S—.

The term "lower-alkylsulfinyl" refers to the group R—S(O)—.

The term "lower-alkylsulfonyl" refers to the group R—S(O)₂—.

The term "lower-alkoxysulfonyl" refers to the group RO—S(O)₂—.

The term "hydroxysulfonyl" refers to the group HO—S(O₂)—.

The term "aryl" refers to an aromatic monovalent mono- or poly- carbocyclic radical, which can optionally be mono-, di-, or tri-substituted, independently, with hydrogen, hydroxyl, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl.

The term "(lower-alkyl)-hydroxylmethyl" refers to the group —CH(OH)—(lower-alkyl).

The term "arylmethyl" refers to the group aryl-CH₂-, e.g., benzyl.

The term "pyridylmethyl" refers to the groups, 4-pyridylmethyl, 3-pyridylmethyl or 2-pyridylmethyl.

The term "tetrazolyl" refers to the group

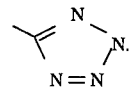

The term "electron withdrawing group" refers to a radical group that has a greater affinity for electrons than a hydrogen atom would if it occupied the same position in the molecule. For example, typical electron withdrawing groups are halo (e.g., chloro, bromo, iodo and fluoro), nitro, trifluoromethyl, cyano, carboxy, methoxycarbonyl and methylcarbonyl.

The term "pharmaceutically acceptable esters" refers to those compounds formed from compounds of Formula I containing a carboxy group when contacted with an alcohol, such as, methanol, ethanol or propanol under suitable conditions.

The term "pharmaceutically acceptable ethers" refers to those compounds formed from compounds of Formula I containing a hydroxy group when contacted with a suitable reagents (e.g., alkyl halide) under suitable conditions.

The term "esterification reagent" refers to a reagent (e.g., diazomethane, methanol, methyl iodide, ethyl iodide or ethanol) that when contacted with a carboxy group under suitable circumstances results in the formation of the corresponding alkoxycarbonyl group.

The term "compound", as used in the detailed description and in the claims (particularly the dependent claims) in reference to a compound of Formula I, is intended to refer to the pharmaceutically acceptable salts, esters, or ethers of the compound, unless expressly stated otherwise, such as "the compound of Formula I as a free base".

The term "pharmaceutically acceptable salt" refers to any salt derived from an inorganic or organic acid or base.

The term "pharmaceutically acceptable anion" refers to the anion of such acid addition salts. The term "pharmaceutically acceptable cation" refers to the cation of such base addition salts. The salt, anion and/or the cation are chosen not to be biologically or otherwise undesirable. The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like. The cations are derived from bases, such as alkaline earth hydroxides, including calcium hydroxide, potassium hydroxide, sodium hydroxide, lithium hydroxide and the like.

As used herein, the term "allograft rejection" refers to the humoral or cellular immune response mounted by the immune system of a mammal after it has received a histo-incompatible tissue graft from another mammal of the same species, thereby producing tissue injury to the graft in such a recipient.

As used herein, the term "graft-vs-host disease" refers to the immune response that originates from transplanted graft tissue, in particular, transplanted bone-marrow tissue, and that is directed towards the host tissue, thereby producing tissue injury in the host.

As used herein, the term "autoimmune disease" refers to disorders wherein the immune system of a mammal mounts a humoral or cellular immune response to the mammal's own tissue or to antigenic agents that are not intrinsically harmful to the mammal, thereby producing tissue injury in such a mammal. Examples of such disorders include, but are not limited to, systemic lupus erythematosus, rheumatoid arthritis and type I diabetes.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms. The conditions and diseases treated in the present invention include, inflammation, pain, pyrexia, autoimmune disease, allograft rejection, graft-vs-host, disease, allergies and uveitis.

As used herein, the term "therapeutically effective amount" refers to that amount of a compound of Formula I which, when administered to a mammal in need thereof, is sufficient to effect treatment (as defined above) as an anti-inflammatory agent, immunosuppressive agent, anti-allograft rejection agent, anti-graft-vs-host disease agent, anti-allergy agent, autoimmune disease agent or analgetic agent. The amount that constitutes a "therapeutically effective amount" will vary depending on the compound, the condition or disease and its severity, and the mammal to be treated, but may be determined routinely by one of ordinary skill in the art with regard to contemporary knowledge and to this disclosure.

As used herein, the term "q.s." means adding a quantity sufficient to achieve a stated function, e.g., to bring a solution to a desired volume (e.g., 100 mL).

As used herein, the term "mp" refers to melting point. All temperatures are given in degrees Celsius (i.e., °C.)

Unless specified to the contrary, the reactions described herein take place at atmospheric pressure over a temperature range from about −78° C. to about 150° C., more preferably from about 10° C. to about 50° C., and most preferably at about room (or "ambient") temperature, e.g., about 20° C. Unless specified to the contrary, the ranges of time and temperature described herein are approximate, e.g., "from 8 to 24 hours at from 10° C. to 100° C." means from about 8 to about 24 hours at about 10° C. to about 100° C.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

The following numbering and nomenclature system will be used for naming the compounds of the invention.

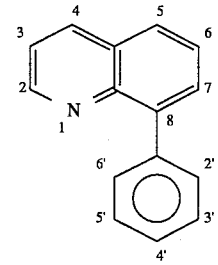

Some representative compounds are named in the following examples.

The compound of Formula I where $R^1$ is isopropyl, $R^3$ is nitro, and $R^2$, $R^4$, $R^5$, and $R^6$ are hydrogen can be named 6-isopropyl-8-(3-nitrophenyl)quinoline.

The compound of Formula I where $R^1$ is 4-pyridylmethyl, $R^3$ is nitro, and $R^2$, $R^4$, $R^5$, and $R^6$ are hydrogen can be named 6-(4-pyridylmethyl)-8-(3-nitrophenyl)quinoline.

The compound of Formula I where $R^1$ is 4-pyridylmethyl, $R^3$ is chloro, $R^4$ is fluoro, and $R^2$, $R^5$, and $R^6$ are hydrogen can be named 6-(4-pyridylmethyl)-8-(3-chloro-4-fluorophenyl)quinoline.

The compound of Formula I where $R^1$ is isopropyl, $R^4$ is chloro, and $R^2$, $R^3$, $R^5$, and $R^6$ are hydrogen can be named 6-(isopropyl)-8-(4-chlorophenyl)quinoline.

The compound of Formula I where $R^1$ is 4-hydroxybenzyl, $R^2$ is cyano and $R^3$, $R^4$, $R^5$ and $R^6$ are hydrogen can be named 6-(4-hydroxybenzyl)-8-(2-cyanophenyl)quinoline.

The compound of Formula I where $R^1$ is cyclopentylmethyl, $R^3$ is methyl and $R^2$, $R^4$, $R^5$ and $R^6$ are hydrogen can be named 6-cyclopentylmethyl-8-(3-methylphenyl)quinoline.

SYNTHESIS OF THE COMPOUNDS OF FORMULA I

As used in the Reaction Schemes, $R^1$, $R^2$, $R^3$, $R^4$, $R^5$, and $R^6$ are the same as described in the Summary of the Invention.

Reaction Scheme A illustrates the preparation of novel optionally substituted 6,8-quinolines, i.e., the compounds of Formula I.

Reaction Scheme B illustrates an alternate preparation of novel optionally substituted 6,8-quinolines, i.e., the compounds of Formula I, where the final two steps in Reaction Scheme A are carried out in reverse order.

Reaction Scheme C illustrates the preparation of novel optionally substituted 6-(lower alkyl)-hydroxylmethyl)-8-quinolines, and 6-formyl-8-quinolines, i.e., the compounds of Formula I where $R^1$ is formyl, or (lower alkyl)-hydroxylmethyl.

REACTION SCHEME A

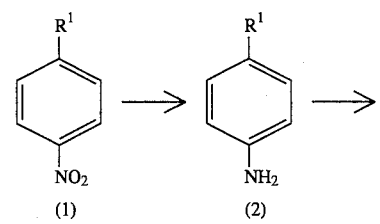

-continued
REACTION SCHEME A

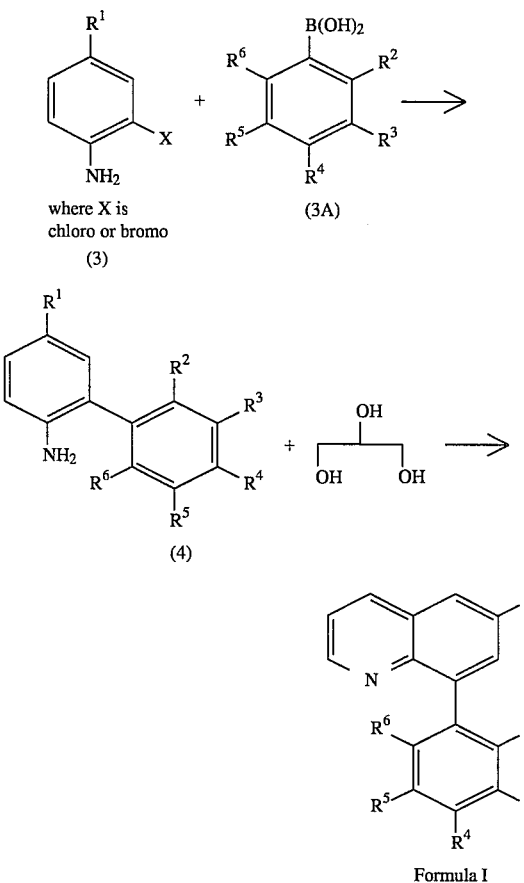

Starting Materials

Referring to Reaction Schemes A, B and C, the compounds of Formula 1 (i.e., 4-optionally substituted-nitrobenzene) and Formula 2 (i.e., 4-optionally substituted aniline) are commercially available from Aldrich Chemicals Co., Inc., Fluka Chemical Corporation, Lancaster Synthesis Ltd., Karl Industries, Maybridge Chemical Co. Ltd. or Tokyo Kasai International. The compounds of Formula 3A, i.e., optionally substituted benzene boronic acid, are commercially available from Lancaster Synthesis Ltd., or alternatively can be prepared following the procedures in Organic Synthesis, Coll Vol 4. Those compounds that are not commercially available can be prepared by one of ordinary skill in art following procedures set forth in references such as, "Fieser and Fieser's Reagents for Organic Synthesis", Volumes 1–15, John Wiley and Sons, 1991; "Rodd's Chemistry of Carbon Compounds", Volumes 1–5 and Supplementals, Elsevier Science Publishers, 1989; and "Organic Reactions", Volumes 1–40, John Wiley and Sons, 1991.

Preparation of Formula 2

An optionally substituted p-nitrobenzene is combined with about 5 molar equivalents of a reducing agent, such as, $SnCl_2.H_2O$, Fe/acetic acid, palladium on carbon/$H_2$, preferably $SnCl_2.H_2O$, in a solvent (10 mL/molar equivalent) such as, ethanol, and ethyl acetate, preferably, ethanol. The solution is heated, the temperature and duration will vary according to the reagent and solvent used, e.g., using ethanol and $SnCl_2.H_2O$, the solution is heated at a temperature in the range of about 50° C. to 90° C., preferably about 70° C., for a period of about 1 hour to 3 hours, preferably about 2 hours. The progress of the reaction is monitored by TLC (thin layer chromatography). When the starting material has been converted to the desired product, the solution is allowed to cool to about room temperature and is neutralized (pH of about 7 to 8). If there are any solids in the solution, they are filtered out, the solution is then extracted with ethyl acetate. The organic layer is isolated and evaporated to dryness. The residue is triturated with a solvent, such as ethyl ether. The solvent is removed yielding the desired optionally substituted p-aminobenzene compound (i.e., a compound of Formula 2).

Preparation of Formula 3

A solution of about 1 molar equivalent of a halogenating agent, such as, N-bromosuccinimide (NBS), or N-chlorosuccinimide (NCS), preferably N-bromosuccinimide, in about 1 mL/molar equivalent of a solvent, preferably DMF is added in a gradual manner to a solution of an optionally substituted p-aminobenzene compound (Formula 2) dissolved in about 10 mL/molar equivalent of a solvent (such as DMF, preferably DMF). The reaction mixture is stirred at about room temperature for a period of about 1 to 5 hours, preferably about 3 hours. The reaction is monitored by TLC. When the reaction is completed, the reaction mixture is combined with $H_2O$ (about 100 mL/molar equivalent) with stirring. The product is isolated as a solid from the solution and washed with $H_2O$. The product is further purified by dissolving in ethyl acetate, treated with brine, dried and triturated with ethyl ether yielding the desired optionally substituted p-amino-m-halobenzene compound (i.e., a compound of Formula 3 where X is chloro or bromo).

Preparation of Formula 4

An optionally substituted p-amino-m-halobenzene compound (Formula 3) is combined with about 1 to 5 molar equivalent, preferably about 2 molar equivalent, of an optionally substituted benzene boronic acid, i.e., Formula 3A (where $R^2$, $R^3$, $R^4$, $R^5$, and $R^6$ are as described in the Summary of the Invention), 2M $Na_2CO_3$ (about 4 molar equivalent), methanol or ethanol, preferably methanol (about 6.5 mL/molar equivalent), and benzene or toluene, preferably benzene (about 32 mL/molar equivalent). To this solution is added about 0.01 to 0.1 molar equivalent, preferably about 0.035 molar equivalent of palladium tetrakis triphenylphosphine. The reaction mixture is heated to about reflux for a period of about 3 to 9 hours, preferably about 6 hours. The progress of the reaction is monitor by TLC. Upon completion of the reaction, the mixture is allowed to cool to about room temperature, and the solvents removed. About 40 mL/molar equivalent of ethyl acetate is added to the residue and filtered through a drying agent (e.g., $Na_2SO_4$), the product is isolated by chromatography, preferably, preparative thin layer chromatography, yielding the desired optionally substituted p-amino-m-arylbenzene compound (e.g., a compound of Formula 4).

Preparation of Formula I

An optionally substituted p-amino-m-arylbenzene compound (Formula 4) is combined with about 1 molar equivalent of an oxidant, such as, ferric oxide, m-nitrobenzenesulphonic acid, nitrobenzene or arsenic pentoxide, preferably arsenic pentoxide, and 3 molar equivalent of glycerol under an inert atmosphere. The mixture is heated to a temperature in the range of about 75° C. to 125° C., preferably about 100° C., for a period of about 15 minutes to 45 minutes, preferably about 30 minutes. About 12 molar equivalent of a concentrated acid (preferably concentrated $H_2SO_4$) is added to the mixture in a gradual manner, and the mixture is heated to a temperature in the range of about 100° C. to 200° C., preferably about 150° C. for a period of about 1 to 3 hours, preferably about 2 hours. The progress of the reaction is monitored by TLC (9:1 hexane:ethyl acetate, worked up by adding $H_2O$ and basifying with $NH_4OH$, and extracting into ethyl acetate). When TLC indicates that about 90% or greater of the starting material has been converted, the heat is removed from the reaction mixture. Ice (about 0.5 gm/molar equivalent) is added to the reaction mixture, and the resulting solution is basified with $NH_4OH$. The resulting precipitate is isolated, washed with $H_2O$, and air dried. The dried solid is further purified by extraction, filtration and chromatography yielding the desired 6-optionally substituted-8-aryl-quinoline compound (i.e., a compound of Formula I).

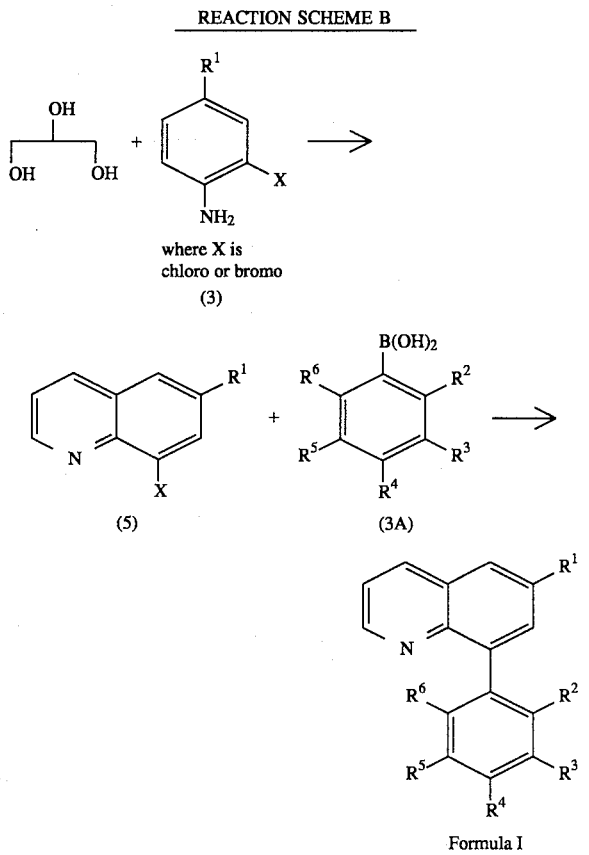

REACTION SCHEME B where X is chloro or bromo
(3)

(5)

(3A)

Formula I

Preparation of Formula 5

An optionally substituted p-amino-m-halobenzene compound (Formula 3) combined with about 1 molar equivalent of arsenic pentoxide and 3 molar equivalent of glycerol under an inert atmosphere. The mixture is heated to a temperature in the range of about 75° C. to 125° C., preferably about 100° C., for a period of about 15 minutes to 45 minutes, preferably about 30 minutes. About 12 molar equivalent of a concentrated acid (preferably concentrated $H_2SO_4$) is added to the mixture in a gradual manner, and the mixture is heated to a temperature in the range of about 100° C. to 200° C., preferably about 150° C. for a period of about 1 to 3 hours, preferably about 2 hours. The progress of the reaction is monitored by TLC (9:1 hexane:ethyl acetate, worked up by adding $H_2O$ and basifying with $NH_4OH$, and extracting into ethyl acetate). When TLC indicates that about 90% or greater of the starting material has been converted, the heat is removed from the reaction mixture. Ice (about 0.5 gm/molar equivalent) is added to the reaction mixture, and the resulting solution is basified with $NH_4OH$. The resulting precipitate is isolated, washed with $H_2O$, and air dried. The dried solid is further purified by extraction, filtration and chromatography yielding the desired 6-optionally substituted-8-haloquinoline compound (i.e., a compound of Formula 5).

Preparation of Formula 3A

About 2 molar equivalents of trimethylborate is dissolved in 4.16 mL/molar equivalent of an apolar solvent (such as, diethyl ether, or tetrahydrofuran, preferably diethyl ether) and cooled to a temperature in the range of about −50° to −80° C., preferably about −65° C. An optionally substituted phenyl grignard reagent is added to the solution in a gradual (e.g., dropwise) manner of a period of about 20 minutes/ molar equivalent. The mixture is then stirred at a temperature in the range of about −50° C. to −80° C. for about 15 to 45 minutes, preferably about 30 minutes. The mixture is allowed to warm to about −10° C. to 10° C., preferably about 0° C. and stirred for a period of about 1 hour. $H_2O$ is added to the reaction mixture (about 25 mL/molar equivalent) and stirred for a period of about 1 hour. The organic layer is removed and the residue is extracted (e.g., 3× ethyl acetate). The organic layers are combined, worked up, and dried over a drying agent (e.g., $MgSO_4$). The solution is concentrated, hexanes are added to the solution (about 100 mL/molar equivalent) and the solution is stirred for a period of about 1 hour until a free flowing suspension forms. The suspension is filtered and air dried. The resultant optionally substituted benzene boronic acid (i.e., a compound of Formula 3A) is carried on to the next step of the process.

Preparation of Formula I

An 6-optionally substituted-8-haloquinoline compound (i.e., a compound of Formula 5) is combined with about 2 molar equivalent of an optionally substituted benzene boronic acid, i.e., Formula 3A (where $R^2$, $R^3$, $R^4$, $R^5$, and $R^6$ are as described in the Summary of the Invention), 2M $Na_2CO_3$ (about 4 molar equivalent), methanol (about 6.5 mL/molar equivalent), and benzene (about 32 mL/molar equivalent). To this solution is added about 0.1 molar equivalent of palladium tetrakis triphenylphosphine. The reaction mixture is heated to about reflux for a period of about 3 to 9 hours, preferably about 6 hours. The progress of the reaction is monitor by TLC. Upon completion of the reaction, the mixture is allowed to cool to about room temperature, and the solvents removed. About 40 mL/molar equivalent of ethyl acetate is added to the residue and filtered through a drying agent (e.g., $Na_2SO_4$), the product is isolated by chromatography, preferably, preparative thin layer chromatography, yielding the desired 6-optionally substituted-8-aryl-quinoline compound (i.e., a compound of Formula I).

REACTION SCHEME C

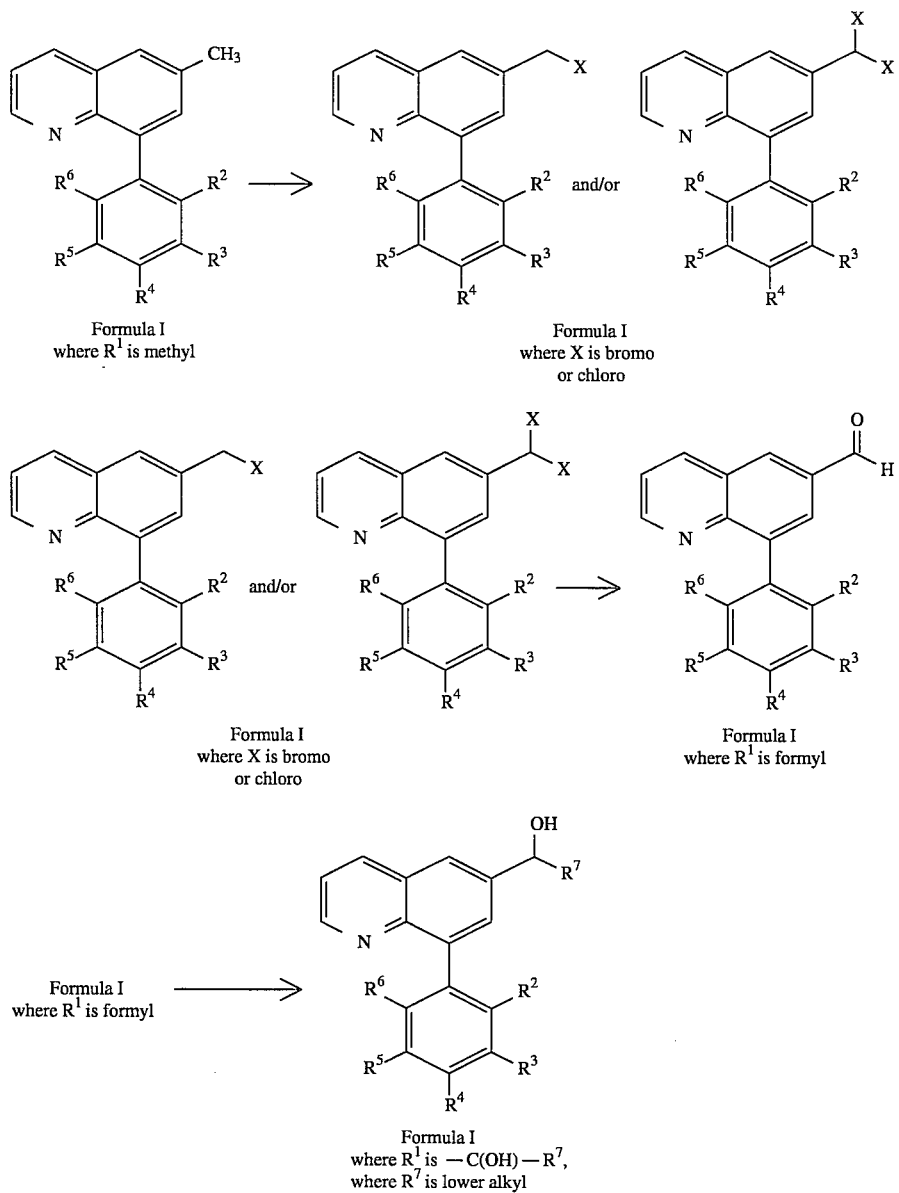

Preparation of Formula I Where $R^1$ Is —$CH_2$—X and/or —CH—$X_2$

A 6-methyl-8-optionally substituted phenyl-quinoline (i.e., a compound of Formula I where $R^1$ is methyl, prepared according procedures described in Reaction Scheme A or B) is dissolved in a solvent such as carbon tetrachloride (about 4 mL/molar equivalent) and heated to reflux. About 1 molar equivalent of a halogenating reagent, such as N-bromosuccinamide (NBS) or N-chlorosuccinamide (NCS), preferably N-bromosuccinamide and about 0.2 molar equivalent of 2,2'-azobis( 2-methylpropionitrile) are added to the refluxing solution. The reaction mixture is optionally exposed to light (e.g., 250 W light bulb) for a period of about 30 minutes to 90 minutes, preferably about 1 hour. The reaction mixture is then stirred for a period of about 1 to 3 hours, preferably about 2 hours. The progress of the reaction is monitored by chromatography. Upon conversion greater than about 90% of the starting material, the reaction solution is cooled to about 0° C., then poured through a drying agent, such as, $Na_2SO_4$. The solution is concentrated yielding the mono- and di-halogenated products (i.e., Formula I, where $R^1$ is —$CH_2$—X and —CH—$X_2$) which are taken on to the next step without further purification or isolation.

Preparation of Formula I Where $R^1$ Is Formyl

The mono and dihalogenated quinoline mixture from the previous step was dissolved in a solvent, such as methylene chloride or chloroform, preferably chloroform (about 4.5 mL/molar equivalent) and added in a gradual manner to an oxidizing reagent, such as, about 5 molar equivalents of tetra n-butylammonium dichromate in a solvent, such as methylene chloride or chloroform, preferably chloroform (about 5.5 mL/molar equivalent). The reaction mixture is heated, preferably to reflux temperature, and refluxed for about 2 to 6 hours, preferably about 4 hours. The reaction mixture is allowed to cooled to about room temperature and filtered, preferably through a silica gel pad. The residue is eluted with an ether, preferably diethyl ether, and isolated and purified by chromatography to obtain the desired 6-formyl-8-(optionally substituted phenyl)quinoline (i.e., Formula I where $R^1$ if formyl). Alternatively the mono and di-halogenated quinoline mixture can be oxidized by the Kornblum oxidation [Chem Rev, Vol 67, No. 3, (1967), p 247–260] or the Sommelet oxidation [Org. React., Vol 8, p 197–217 (1954)].

Preparation of Formula I Where $R^1$ Is
—CH(OH)-(Lower Alkyl)

A 6-formyl-8-(optionally substituted phenyl)quinoline is dissolved in a nonpolar solvent, preferably tetrahydrofuran (about 6.66 mL/molar equivalent) and cooled to a temperature in the range of about −50° C. to −100° C., preferably about −78° C. To this solution is added an alkylation reagent, such as a lower-alkyl grignard reagent, or a lower-alkyl lithium reagent (about 1 to 3 molar equivalent, preferably about 2 molar equivalent) in a gradual manner (about 1.66 minutes/molar equivalent). The reaction mixture is stirred for period of about 10 to 30 minutes, preferably about 20 minutes. The reaction mixture is quenched with an aqueous salt solution, preferably saturated ammonium chloride (about 16 mL/molar equivalent). The desired product is purified by extraction (preferably with ethyl acetate), and drying (preferably over $MgSO_4$). The residue is further purified and isolated by chromatography to yield the desired optionally substituted 6-(hydroxy lower-alkyl)-8-(optionally substituted phenyl)quinoline, i.e., Formula I where $R^1$ is (lower alkyl)hydroxylmethyl.

Preparation of the Salt of Formula I

The pharmaceutically acceptable salts of Formula I are prepared by dissolving a compound of Formula I in a suitable solvent (such as methanol, dioxane or diethyl ether) adding 1 to 3 molar equivalents (preferably about two molar equivalent) of an appropriate acid (such as hydrochloric gas) or base (such as an alkaline earth hydroxide, e.g., lithium hydroxide, calcium hydroxide, potassium hydroxide, sodium hydroxide or the like; preferably sodium hydroxide) and stirring. The salt is isolated by lyophilization or by precipitation, using techniques that will be apparent to those skilled in the art.

Preparation of N-oxides of Formula I

A compound of Formula I, where $R^1$ is pyridylmethyl (e.g., 4-pyridylmethyl, 3-pyridylmethyl or 2-pyridylmethyl), is converted to the corresponding N-oxide derivative by treating with an oxidizing agent (e.g., m-chloroperoxybenzoic acid) in a solvent (e.g., methylene chloride) and stirred for a period of about 30 to 90 minutes, preferably about 60 minutes at a temperature in the range of about 0° C. to 50° C., preferably about room temperature. Following the reaction, the desired product is isolated and purified by preparative thin-layer chromatography.

PREFERRED COMPOUNDS

Presently preferred are the compounds of Formula I where $R^3$ is an electron withdrawing group.

Especially preferred is the compound of Formula I where $R^3$ is nitro.

Also especially preferred is the compound of Formula I where $R^3$ is chloro.

Also especially preferred is the compound of Formula I where $R^3$ is chloro and $R^4$ is fluoro.

Of the compound where $R^3$ is nitro most preferred is the compound of Formula I where and $R^1$ is 4-pyridylmethyl or benzyl or isopropyl.

Of the compound where $R^3$ is chloro most preferred is the compound of Formula I where and $R^1$ is 4-pyridylmethyl or isopropyl.

Of the compound where $R^3$ is chloro and $R^4$ is fluoro most preferred is the compound of Formula I where $R^1$ is isopropyl or methyl.

PREFERRED PROCESSES AND LAST STEPS

A preferred process for making 6-optionally substituted 8-aryl-quinolines by combining the corresponding optionally substituted benzene boronic acid with the corresponding 6-optionally substituted quinoline.

Another preferred process for making 6-optionally substituted 8-aryl-quinolines by combining the corresponding optionally substituted p-amino-m-benzene with glycerol and arsenic pentoxide.

UTILITY, TESTING AND ADMINISTRATION

General Utility

The compounds of this invention, including the pharmaceutically acceptable esters, ethers, N-oxides or salts thereof, and the compositions containing them are particularly useful as anti-inflammatory, immunosuppressive, anti-allograft rejection, anti-graft-vs-host disease, anti-allergic agents (e.g., asthma, rhinitis and atopic dermatitis), bronchiodilation agents, anti-autoimmune disease or analgetic agents. The compounds of this invention act as PDE IV selective inhibitors, thereby modulating cAMP levels. Thus, these compounds are of use for the treatment of cAMP related conditions or diseases, particularly those that are modulated by leukocyte cAMP.

For example, inflammation, autoimmune diseases, graft-vs-host disease and allograft rejection are conditions that are manifested by the proliferation of lymphocytes. The proliferation is triggered by the presence of cAMP at specific levels. Inhibition of lymphocyte proliferation is accomplished by increasing levels of cAMP resulting from the inhibition of lymphocyte phosphodiesterase.

Testing

Potency and selectivity of compounds as inhibitors of PDE IV is determined by following, for example, the procedures described in Example 23, or modifications thereof.

The immunomodulatory and anti-inflammatory activity of the compounds of the invention can be determined by a variety of assays utilizing both in vitro and in vivo procedures.

Inhibition of the proliferation of lymphocytes in response to mitogenic stimulation is determined by the procedures described by Greaves, et al. ["Activation of human T and B lymphocytes by polyclonal mitogens," Nature, 248, 698–701 (1974)], or modifications thereof (see, Example 24).

Inhibition of lymphocyte activation in response to antigenic challenge is determined in vitro by inhibition of a cytolytic T-cell assay (CTL) as described by Wunderlich, et al., Nature (1970), Vol. 228, p. 62, or a modification thereof.

Immune modulation is determined by in vivo procedures utilizing the Jerne Hemolytic Plaque Assay, [Jerne, et al., "The agar plaque technique for recognizing antibody producing cells," Cell-bound Antibodies, Amos, B and Kaprowski, H. editors (Wistar Institute Press, Philadelphia) 1963, p. 109] or a modification thereof (see, Example 25).

Anti-inflammatory activity is determined by the Arachidonic Acid-Induced Mouse Ear Edema Assay [Young, et al., J. Invest. Derm., 82:367–371 (1984)] (see, Example 26).

Anti-inflammatory activity is also determined by the Adjuvant Arthritis assay [Pearson, C. M., Proc. Soc. Exp. Biol. Med., 91:95–101 (1956)], or modifications thereof (see Example 27).

Anti-autoimmune activity in treating autoimmune disease can be determined utilizing the survivability of MRL/lpr mice described by Theofilopoulos, et al., Advances in Immunology, Vol 37, pages 269–390 (1985) on pages 274–276, or a modification thereof (see Example 28).

Analgetic activity is determined by the Phenylquinone-induced Mouse Writhing Assay [Hendershot, et al., J. Pharmacol. Exp. Ther., 125:237–240 (1959)] (see Example 29).

Administration

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art.

Administration can be via any accepted systemic or local route, for example, via parenteral, oral (particularly for infant formulations), intravenous, nasal, bronchial inhalation (i.e., aerosal formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Intravenous Administration

Intravenous injection has proven to be an important route of administration for therapeutic agents. The compounds of the present invention can be administered via this route, for example, by dissolving the compound, ester, ether, N-oxide or salt in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

Oral Administration

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

Aerosol Administration

Aerosol administration is an effective means for delivering a therapeutic agent directly to the respiratory tract. Some of the advantages of this method are: 1) it circumvents the effects of enzymatic degradation, poor absorption from the gastrointestinal tract, or loss of the therapeutic agent to the hepatic first-pass effect; 2) it administers therapeutic agents which would otherwise fail to reach their target sites in the respiratory tract due to their molecular size, charge or affinity to extra-pulmonary sites; 3) it provides for fast absorption into the body via the aveoli of the lungs; and 4) it avoids exposing other organ systems to the therapeutic agent, which is important where exposure might cause undesirable side effects. For these reasons, aerosol administration is particularly advantageous for treatment of asthma, local infections of the lung, and other diseases or disease conditions of the lung and respiratory tract.

There are three types of pharmaceutical inhalation devices, nebulizers inhalers, metered-dose inhalers (MDI) and dry powder inhalers (DPI). Nebulizer devices produce a stream of high velocity air that causes the therapeutic agent (which has been formulated in a liquid form) to spray as a mist which is carried into the patient's respiratory tract. MDIs typically have the formulation packaged with a compressed gas. Upon actuation, the device discharges a measure amount of therapeutic agent by compressed gas, thus affording a reliable method of administering a set amount of agent. Historically, MDIs have used chlorofluorocarbons (CFC) as the compressed gas to propel the therapeutic agent. In recent years, CFCs have been linked with the depletion of the earth's ozone layer. As a result of this, alternative propellants that are non-ozone threatening are being sought out as potential replacements for CFCs.

DPIs administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to with each actuation. Examples of DPIs being used are Spinhaler® (for the administration of disodium cromoglycate), Rotahaler® (for albuterol) and Turbuhaler® (for terbutaline sulfate). All of the above methods can be used for administering the present invention, particularly for the treatment of asthma and other similar or related respiratory tract disorders.

Liposomal Formulations

Pharmaceutical formulations based on liposomes have recently reached human clinical trials. Their benefits are believed related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., J. Infect. Dis., 151:704–710 (1985); Gotfredsen et al., Biochemical Pharmacology, 32:3389–3396 (1983)]; or to the reticuloendothelial system [see Eppstein et al., Int. J. Immunotherapy, 2:115–126 (1986)], to increase duration of drug action [see: Gabizon et al., Cancer Res., 42:4734 (1982); Eppstein et al., Delivery Systems for Peptide Drugs, Eds. S. S. Davis, L. Illum and E. Tomlinson, Plenum Pub. Corp., New York, pp. 277–283; C. A. Hunt, Biochemica et Biophysica Acta., 719:450–463 (1982); and Senior et al., Biochemica et Biophysica Acta., 839:1–8 (1985)], or to divert a drug away from organs that are particularly sensitive to its toxic effects [see: Weinstein et al., Pharmac. Ther., 24:207–233 (1983); Olson et al., Eur. J. Cancer Clin. Oncol., 18:167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing are incorporated herein by reference.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see Remington's Pharmaceutical Sciences, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and to practice the present invention. They should not be considered as limiting the scope of the invention, but merely as being illustrative and representative thereof.

EXAMPLE 1

Preparation of 4-(4-Aminobenzyl)pyridine

1A. Formula 2, Where $R^1$ is 4-Pyridylmethyl 4-(4-Nitrobenzyl)pyridine (214.22 mg) was combined with absolute ethanol (10 mL) and $SnCl_2.2H_2O$ (225.63 mg). The reaction mixture was heated to 70° C. under nitrogen for 2 hours. The progress of the reaction was monitored by thin-layer chromatography (an aliquot of the mixture was collected, neutralized with saturated $NaHCO_3$ to pH 7–8, extracted into ethyl acetate). When all of the starting material had been converted, the reaction mixture was allowed to cool to room temperature, neutralized with saturated $NaHCO_3$ to pH 7–8 and extracted with ethyl acetate. The organic layers were collected and dried of MgSO$_4$. The solvents were removed and the residue was triturated with ethyl ether. The desired product, i.e., 4-(4-aminobenzyl)pyridine, was filtered out of the solution as cream colored crystals and air dried.

Characteristic analytical data are as follows: mp 159.1° C.–160.3° C.; and elemental analysis [calc(found)] C: 78.2 (78.12), H: 6.56 (6.45), and N: 15.20 (15.33).

1B. Compounds of Formula 2, Where R$^1$ Is Varied

Other desired compounds of Formula 2 can be prepared by following the procedures described in Example 1A, and using different starting compounds. For example, 4-isopropylnitrobenzene can be converted to 4-isopropylaniline,
4-methylnitrobenzene can be converted to 4-methylaniline,
4-benzylnitrobenzene can be converted to 4-benzylaniline,
4-ethylnitrobenzene can be converted to 4-ethylaniline,
4-(3-propenyl)nitrobenzene can be converted to 4-(3-propenyl)aniline,
4-propylnitrobenzene can be converted to 4-propylaniline,
4-butylnitrobenzene can be converted to 4-butylaniline,
4-pentylnitrobenzene can be converted to 4-pentylaniline,
4-hexylnitrobenzene can be converted to 4-hexylaniline,
4-methoxynitrobenzene can be converted to 4-methoxyaniline,
4-ethoxynitrobenzene can be converted to 4-ethoxyaniline,
4-trifluoromethylnitrobenzene can be converted to 4-trifluoromethylaniline,
4-(3-pyridylmethyl)nitrobenzene can be converted to 4-(3-pyridylmethyl)aniline,
4-(2-pyridylmethyl)nitrobenzene can be converted to 4-(2-pyridylmethyl)aniline,
4-(cyclopentylmethyl)nitrobenzene can be converted to 4-(cyclopentylmethyl)aniline,
4-(cyclopropylmethyl)nitrobenzene can be converted to 4-(cyclopropylmethyl)aniline,
4-(thiomethyl)nitrobenzene can be converted to 4-(thiomethyl)aniline, and
4-(methylsulfonylmethyl)nitrobenzene can be converted to 4-(methylsulfonylmethyl)aniline.

EXAMPLE 2

Preparation of 4-(4-Amino-3-Bromobenzyl)pyridine

2A. Formula 3, Where R$^1$ is 4-Pyridylmethyl

A solution of N-bromosuccinimide (1.4 gm) in 10 mL dimethylformamide was added in a dropwise manner to a solution of 4-(4-aminobenzyl)pyridine (1.5 gm) in 10 mL of dimethylformamide. The reaction flask was wrapped in aluminum foil to prevent exposure of the reagents to light. The reaction mixture was stirred at room temperature for 3 hours. The progress of the reaction was monitored by thin-layer chromatography. When the reaction was completed, the reaction mixture was combined with 100 mL of H$_2$O with stirring. A reddish brown precipitate was formed, filtered out of solution, washed with H$_2$O, and air dried. The solid was dissolved in ethyl acetate, back washed with saturated NaCl, dried over MgSO$_4$ and triturated with ethyl ether. The solid was filtered from the solution and air dried yielding 1.6 gm of 4-(4-amino-3-bromobenzyl)pyridine as reddish/tan crystals.

Characteristic analytical data are as follows: mp 102.7° C.–103.9° C.;

2B. Other Prepared Compounds of Formula 3, Where R$^1$ Is Varied

Other compounds of Formula 3 were also prepared following the procedures described in Example 2A, and substituting 4-(4-aminobenzyl)pyridine with different starting compounds. For example, following is a list of starting compounds and the corresponding desired compounds that were obtained by following the above-referenced procedure:

4-isopropylaniline was converted to 2-bromo-4-isopropylaniline,
4-methylaniline was converted to 2-bromo-4-methylaniline,
4-benzylaniline was converted to 4-benzyl-2-bromoaniline, and
4-(4-pyridylmethyl)aniline was converted to 2-bromo-4-(4-pyridylmethyl)aniline.

2C. Compounds of Formula 3, Where R$^1$ Is Varied

In addition, other desired compounds of Formula 3 can be prepared by following the procedures described in Example 2A, and using different starting compounds. For example, 4-ethylaniline can be converted to 2-bromo-4-ethylaniline,
4-(3-propenyl)aniline can be converted to 2-bromo-4-(3-propenyl)aniline,
4-propylaniline can be converted to 2-bromo-4-propylaniline,
4-butylaniline can be converted to 2-bromo-4-butylaniline,
4-pentylaniline can be converted to 2-bromo-4-pentylaniline,
4-hexylaniline can be converted to 2-bromo-4-hexylaniline,
4-methoxyaniline can be converted to 2-bromo-4-methoxyaniline,
4-ethoxyaniline can be converted to 2-bromo-4-ethoxyaniline,
4-trifluoromethylaniline can be converted to 2-bromo-4-trifluoromethylaniline,
4-(3-pyridylmethyl)aniline can be converted to 2-bromo-4-(3-pyridylmethyl)aniline,
4-(2-pyridylmethyl)aniline can be converted to 2-bromo-4-(2-pyridylmethyl)aniline,
4-(cyclopentylmethyl)aniline can be converted to 2-bromo-4-(cyclopentylmethyl)aniline,
4-(cyclopropylmethyl)aniline can be converted to 2-bromo-4-(cyclopropylmethyl)aniline,
4-(methylthiomethyl)aniline can be converted to 2-bromo-4-(methylthiomethyl)aniline, and
4-(methylsulfonylmethyl)aniline can be converted to 2-bromo-4-(methylsulfonylmethyl)aniline.

EXAMPLE 3

Preparation of 3-Chlorobenzene Boronic Acid

3A. Formula 3A Where R$^3$ is Chloro

A solution of trimethylborate in 200 mL of ethyl acetate was cooled to −65° C. 3-Chlorobenzene magnesium chloride (0.8M, 60 mL), i.e., a grignard reagent, was added to the solution in a dropwise manner over 20 minutes. The mixture was kept in the temperature range of −60° C. to −70° C. and stirred. After 30 minutes, the mixture was allowed to warm to 0° C. and stirred for 1 hour. The mixture was quenched with H$_2$O (25 mL) and stirred at room temperature for 1 hour. The solvent was removed and the remaining mass was extracted ethyl ether (3×100 mL). The organic layers were combined and washed with H$_2$O (2×50 mL), dilute HCl (2×100 mL), H$_2$O (2×50 mL) and brine (1×50 mL). The organic layer was dried with MgSO$_4$, concentrated and allowed to stand. 100 mL of hexanes was added and the solution was stirred for 1 hour. The solution was filtered and allowed to air dry yielding 4.6 g of 3-chlorobenzene boronic acid as a white solid.

3B. Compounds of Formula 3A, Where R$^2$, R$^3$, R$^4$, R$^5$ and R$^6$ are Varied.

Other desired compounds of Formula 3A can be prepared by following the procedures described in Example 3A, and using different starting compounds. For example,
3-nitrobenzene magnesium bromide can be converted to 3-nitrobenzene boronic acid,
3-chloro-4-fluorobenzene magnesium chloride can be converted to 3-chloro-4-fluorobenzene boronic acid,
4-chlorobenzene magnesium chloride can be converted to 4-chlorobenzene boronic acid,
benzene magnesium bromide can be converted to benzene boronic acid,
3,4-dichlorobenzene magnesium bromide can be converted to 3,4-dichlorobenzene boronic acid,
3-bromobenzene magnesium bromide can be converted to 3-bromobenzene boronic acid,
3-trifluoromethylbenzene magnesium bromide can be converted to 3-trifluoromethylbenzene boronic acid,
3-methoxycarbonylbenzene magnesium chloride can be converted to 3-methoxycarbonylbenzene boronic acid.

EXAMPLE 4

Preparation of
4-[4-Amino-3-(3-Nitrophenyl)benzyl]pyridine

4A. Formula 4, Where $R^1$ is 4-Pyridylmethyl, $R^3$ is Nitro, and $R^2$, $R^4$, $R^5$ and $R^6$ are hydrogen.

4-(4-Amino-3-bromobenzyl)pyridine (1.0 gm), 3-nitrobenzene boronic acid (0.63 gm), palladium tetrakis triphenylphosphine (0.47 gm), methanol (6.5 mL), 2.0M Na$_2$CO$_3$ (1.9 mL) and benzene (32 mL) are combined in a reaction flask that is wrapped in aluminum foil (to prevent exposure of the reagents to light). The reaction mixture is heated to reflux for 6 hours. The progress of the reaction is monitored by thin-layer chromatography (9:1 hexane:ethyl acetate). When the starting material is converted, the reaction mixture is allowed to cool and the solvents are removed. Ethyl acetate is added to the residue, the resultant solution is filtered through a pad of Na$_2$SO$_4$, and concentrated. The product is isolated by preparative thin-layer chromatography (9:1 hexane:ethyl acetate) yielding 983 mg of 4-[4-amino-3-(3-nitrophenyl)benzyl] pyridine as an orange oil.

Characteristic analytical data are as follows: ms m/e 305(M+); $^1$H NMR (CDCl$_3$) δ 3.74 (bs, 2H), 3.92 (s, 2H), 6.77 (d, 1H, J=8.1 Hz), 6.95 (d, 1H, J=2.1 Hz), 7.03 (dd, 1H, J=2.1 Hz, J=8.1 Hz), 7.14 (d, 1H, J=5.7 Hz), 7.62 (dd, 1H, J=8.2 Hz, J=7.7 Hz), 7.82 (ddd, 1H, J=7.7 Hz, J=1.9 Hz, J=2.5Hz), 8.21 (ddd, 1H, J=8.2 Hz, J=2.5 Hz, J=1.9Hz), 8.34 (dd, 1H, J=1.9 Hz, J=1.9 Hz), and 8.5 (dd, 1H, J=5.7 Hz).
4B. Other Prepared Compounds of Formula 4, Where $R^1$, $R^2$, $R^3$, $R^4$, $R^5$ and $R^6$ Are Varied Other compounds of Formula 4 were also prepared following the procedures described in Example 4A, and substituting for 4-(4-amino-3-bromobenzyl)pyridine and 3-nitrobenzene boronic acid with different starting compounds. For example, following is a list of starting compounds and the corresponding desired compounds that were obtained by following the above-referenced procedure:
2-bromo-4-isopropylaniline and benzene boronic acid were combined to form 2-phenyl-4-isopropylaniline,
2-bromo-4-isopropylaniline and 3-nitrobenzene boronic acid were combined to form 2-(3-nitrophenyl)-4-isopropylaniline,
4-benzyl-2-bromo-aniline and 3-nitrobenzene boronic acid were combined to form 4-benzyl-2-(3-nitrophenyl)aniline,
2-bromo-4-methylaniline and 3-chloro-4-fluorobenzene boronic acid were combined to form 2-(3-chloro-4-fluorophenyl)- 4-methylaniline,
2-bromo-4-isopropylaniline and 3-chloro-4-fluorobenzene boronic acid were combined to form 2-(3-chloro-4-fluoro)- 4-isopropylaniline,
4-benzyl-2-bromo-aniline and 3-chloro-4-fluorobenzene boronic acid were combined to form 4-benzyl-2-(3-chloro- 4-fluorophenyl)-aniline,
2-bromo-4-(4-pyridylmethyl)aniline and 3-chloro-4-fluorobenzene boronic acid were combined to form 2-(3-chloro-4-fluorophenyl)-4-(4-pyridylmethyl)aniline,
2-bromo-4-methylaniline and 4-chlorobenzene boronic acid were combined to form 2-(4-chlorophenyl)-4-methylaniline,
2-bromo-4-isopropylaniline and 4-chlorobenzene boronic acid were combined to form 2-(4-chlorophenyl)-4-isopropylaniline, and
4-benzyl-2-bromo-aniline and 4-chlorobenzene boronic acid were combined to form 4-benzyl-2-(4-chlorophenyl)aniline.
4C. Compounds of Formula 4, Where $R^1$, $R^2$, $R^3$, $R^4$, $R^5$ and $R^6$ Are Varied In addition, other desired compounds of Formula 4 can be prepared by following the procedures described in Example 4A, and using different starting compounds. For example,
2-bromo-4-ethylaniline and 3-trifluoromethylbenzene boronic acid can be combined to form 2-(3-trifluoromethylphenyl)- 4-ethylaniline,
2-bromo-4-isopropylaniline and 3,4-dichlorobenzene boronic acid can be combined to form 2-(3,4-dichlorophenyl)- 4-aniline,
2-bromo-4-(3-propenyl)aniline and 3-nitrobenzene boronic acid can be combined to form 2-(3-nitrophenyl)-3-propenylaniline,
2-bromo-4-propylaniline and 3-nitrobenzene boronic acid can be combined to form 2-(3-nitrophenyl)-4-propylaniline,
2-bromo-4-(n-butyl)aniline and 3-nitrobenzene boronic acid can be combined to form 2-(3-nitrophenyl)-4-propylaniline,
2-bromo-4-(n-hexyl)aniline and benzene boronic acid can be combined to form 2-phenyl-4-(n-hexyl)aniline,
2-bromo-4-pentylaniline and 3-nitrobenzene boronic acid can be combined to form 2-(3-nitrophenyl)-4-pentylaniline,
2-bromo-4-benzylaniline and 3,4-dichlorobenzene boronic acid can be combined to form 2-(3,4-dichlorophenyl)-4-benzylaniline,
2-bromo-4(3-pyridylmethyl)aniline and 3-methoxycarbonylbenzene boronic acid can be combined to form 2-(3-methoxycarbonyl)- 4-(3-pyridylmethyl)aniline,
2-bromo-4(2-pyridylmethyl)aniline and 3-methoxycarbonylbenzene boronic acid can be combined to form 2-(3-methoxyphenyl)- 4(2-pyridylmethyl)aniline,
2-bromo-4-cyclopentylmethylaniline and 3-chlorobenzene boronic acid can be combined to form 2-(3-chlorophenyl)- 4-cyclopentylmethylaniline,
2-bromo-4-cyclopropylmethylaniline and 3-nitrobenzene boronic acid can be combined to form 2-bromo-4-cyclopropylmethylaniline,
2-bromo-4-(methylthiomethyl)aniline and 3-chlorobenzene boronic acid can be combined to form 2-(3-chlorophenyl)- 4-(methylthiomethyl)aniline,
2-bromo-4-(methylsulfonylmethyl)aniline and benzene boronic acid can be combined to form 2-phenyl-4-(methylsulfonylmethyl)aniline, 2-bromo-4-(cyclopentylmethyl)aniline and 2,3-dichlorobenzene boronic acid can be combined to form 2-(2,3-dichlorophenyl)-4-(cyclopentylmethyl)aniline, and 2-bromo-4-(cyclopentylmethyl)aniline and 3-nitrobenzene boronic acid can be combined to form 2-(3-nitrophenyl)-4-(cyclopentylmethyl)aniline.

EXAMPLE 5

Preparation of
6-(4-Pyridylmethyl)-8-(3-Nitrophenyl)quinoline

5A. Formula I, Where $R^1$ is 4-Pyridylmethyl, $R^3$ is Nitro, and $R^2$, $R^4$, $R^5$ and $R^6$ are Hydrogen.

4-[4-Amino-3-(3-nitrophenyl)benzyl]pyridine (600 mg) was combined with glycerol (489 mg) and arsenic pentoxide (325 mg) under nitrogen. The reaction mixture was heated to 100° C. for 30 minutes. Concentrated sulfuric acid (406 mg) was added in a dropwise manner and the reaction mixture was further heated to 150° C. for 2 hours. The reaction was monitored by TLC (9:1, hexane:ethyl acetate) where an aliquot was worked up by adding the product from the reaction to $H_2O$, basifying with $NH_4OH$ and extracting with ethyl acetate. When TLC indicated that greater than 90% of the starting material had been converted, the reaction mixture was removed from the heat, ice (approximately 1 gm) was added, and $NH_4OH$ was added to basify the mixture. A precipitate was filtered out of the mixture, washed with $H_2O$ and air dried. The resulting solid was suspended in hot ethyl acetate and filtered. The filtrate was concentrated and chromatographed by preparative thin-layer chromatography (4:1, hexane:ethyl acetate), the spot with the higher $R_f$ value was isolated yielding 181 mg of 6-(4-pyridylmethyl)-8-(3-nitrophenyl)quinoline as a viscous yellow oil. The product was recrystallized from diethyl ether as a light yellow solid.

Characteristic analytical data are as follows: mp 131° C.–143° C., elemental analysis, calc(found) C: 73.89 (73.90), H: 4.43 (4.50), and N: 12.31 (12.30); $^1H$ NMR $CDCl_3$ δ 4.21 (s, 2H), 7.21 (d, 2H, J=5.9 Hz), 7.48 (dd, 1H, J=8.3 Hz, J=4.2 Hz), 7.6 (d, 1H, J=2 Hz), 7.66 (dd, 1H, J=8 Hz, J=7.7 Hz), 7.7 (d, 1H, J=2Hz), 8.03 (ddd, 1H, J=7.7 Hz, J=1.4 Hz, J=1.2 Hz), 8.2 (dd, 1H, J=8.3 Hz, J=1.7 Hz, J=1.2 Hz), 8.28 (ddd, 1H J=8 Hz, J=1.44 Hz, J=1.2 Hz), 8.55(m, 3H), 8.93 (dd, 1H, J=4.2 Hz, J=1.7 Hz).

5B. Other Prepared Compounds of Formula I, Where $R^1$, $R^2$, $R^3$, $R^4$, $R^5$ and $R^6$ Are Varied Other compounds of Formula I were also prepared following the procedures described in Example 5A, and substituting 4-[4-amino-3-(3-nitrophenyl)benzyl]pyridine with different starting compounds. For example, following is a list of starting compounds and the corresponding desired compounds that were obtained by following the above-referenced procedure:

2-phenyl-4-isopropylaniline was converted to 6-isopropyl-8-phenyl-quinoline as an oil, 2-(3-nitrophenyl)-4-isopropylaniline was converted to 6-isopropyl-8-(3-nitrophenyl)quinoline as an oil, 4-benzyl-2-(3-nitrophenyl)-aniline was converted to 6-benzyl-8-(3-nitrophenyl)quinoline mp 101° C.–103° C.

2-(3-chloro-4-fluorophenyl)-4-methylaniline was converted to 6-methyl-8-(3-chloro-4-fluorophenyl)quinoline, mp 96° C.–114° C., 2-(3-chloro-4-fluoro)-4-isopropylaniline was converted to 6-isopropyl-8-(3-chloro-4-fluorophenyl)quinoline as an oil, 4-benzyl-2-(3-chloro-4-fluorophenyl)-aniline was converted to 6-benzyl-8-(3-chloro-4-fluorophenyl)quinoline as an oil, 2-(3-chloro-4-fluorophenyl)-4-(4-pyridylmethyl)aniline was converted to 6-(4-pyridylmethyl)-8-(3-chloro-4-fluorophenyl)quinoline as an oil, 2-(4-chlorophenyl)-4-methylaniline was converted to 6-methyl-8-(4-chlorophenyl)quinoline, mp 96° C.–98° C., 2-(4-chlorophenyl)-4-isopropylaniline was converted to 6-isopropyl-8-(4-chlorophenyl)quinoline as an oil, and 4-benzyl-2-(4-chlorophenyl)aniline was converted to 6-benzyl-8-(4-chlorophenyl)quinoline as an oil.

5C. Formula I, Where $R^1$, $R^2$, $R^3$, $R^4$, $R^5$ and $R^6$ Are Varied

In addition, other desired compounds of Formula I can be prepared by following the procedures described in Example 5A, and using different starting compounds. For example, 2-(3-trifluoromethylphenyl)-4-ethylaniline can be converted to 6-ethyl-8-(3-trifluoromethylphenyl)quinoline, 2-(3,4-dichlorophenyl)-4-isopropylaniline can be converted to 6-isopropyl-8-(3,4-dichlorophenyl)quinoline, 2-(3-nitrophenyl)-4-(3-propenyl)aniline can be converted to 6-(3-propenyl)-8-(3-nitrophenyl)quinoline, 2-(3-nitrophenyl)-4-propylaniline can be converted to 6-propyl-8-(3-nitrophenyl)quinoline, 2-(3-nitrophenyl)-4-butylaniline can be converted to 6-butyl-8-(3-nitrophenyl)quinoline, 2-(phenyl)-4-hexylaniline can be converted to 6-hexyl-8-(phenyl)quinoline, 2-(3-nitrophenyl)-4-pentylaniline can be converted to 6-pentyl-8-(3-nitrophenyl)quinoline, 2-(3,4-dichlorophenyl)-4-benzylaniline can be converted to 6-benzyl-8-(3,4-dichlorophenyl)quinoline, 2-(3-methoxycarbonylphenyl)-4-(3-pyridylmethyl)-aniline can be converted to 6-(3-pyridylmethyl)-8-(3-methoxycarbonylphenyl)quinoline, 2-(3-methoxycarbonylphenyl)-4-(2-pyridylmethyl)aniline can be converted to 6-(2-pyridylmethyl)-8-(3-methoxycarbonylphenyl)quinoline, 2-(3-chlorophenyl)-6-cyclopentylmethylaniline can be converted to 6-cyclopentylmethyl-8-(3-chlorophenyl)quinoline, 2-(3-nitrophenyl)-4-cyclopropylmethylaniline can be converted to 6-cyclopropylmethyl-8-(3-nitrophenyl)quinoline, 2-(3-chlorophenyl)-4-(methylthiomethyl)aniline can be converted to 6-methylthiomethyl-8-(3-chlorophenyl)quinoline, 2-phenyl-4-(methylsulfonylmethyl)aniline can be converted to 6-methylsulfonylmethyl-8-(phenyl)quinoline, 2-(3,4-dichlorophenyl)-4-(cyclopentylmethyl)aniline can be converted to 6-cyclopentylmethyl-8-(3,4-dichlorophenyl)quinoline, and 2-(3-nitrophenyl)-4-(cyclohexylmethyl)aniline can be converted to 6-cyclohexylmethyl-8-(3-nitrophenyl)quinoline.

EXAMPLE 6

Preparation of 6-Isopropyl-8-bromoquinoline

6A. Formula 5 Where $R^1$ Is Isopropyl

2-Bromo-4-isopropylaniline (3.0 gm) [obtained from Aldrich Chemical Co.], glycerol (2.8 mL) and arsenic pentoxide (3.22 g) were combined and heated to 100° C. $H_2SO_4$ (concentrated, 1.9 mL) was added to the reaction mixture in a dropwise manner. The mixture was then heated to 150° C. for 2.5 hours. The resulting black oil was added in a dropwise manner to a stirring mixture of saturated $NaHCO_3$ (300 mL) and ethyl acetate (100 mL). After completion of the addition, the reaction mixture was stirred for 30 minutes. The reaction mixture was then extracted with ethyl acetate (2× 200 mL). The organic layers were washed with brine, dried over $MgSO_4$, filtered and concentrated. The resulting material was further purified and isolated by chromatography on silica gel (30:70 ethyl acetate/hexanes) which yielded 2.5 g of 8-bromo-6-isopropylquinoline as a brown oil.

Characteristic analytical data are as follows: elemental analysis calc. (found): C 57.62 (57.65), H 4.84 (4.78), and N 5.60 (5.57); $^1H$ NMR ($CDCl_3$) δ 1.34 (d, 6H, J=6.9 Hz), 3.05 (m, 1H, J=6.9 Hz), 7.42 ((dd, 1H, J=4.2 Hz, J=8.3 Hz), 7.57 (d, 1H, J=1.8 Hz), 7.97 (d, 1H, J=1.8 Hz), 8.1 (dd, 1H, J=8.3 Hz, J=1.7 Hz), and 8.9 (dd, 1H, J=4.2 Hz, J=1.7 Hz).

EXAMPLE 7

Preparation of 6-Isopropyl-8-(3-Nitrophenyl)quinoline Hydrochloride

7A. Formula I Where $R^1$ Is Isopropyl, $R^3$ Is Nitro, and $R^2$, $R^4$, $R^5$, and $R^6$ Are Hydrogen.

8-Bromo-6-isopropylquinoline (1.15 g) was dissolved in 46 mL of ethanol/benzene (1:1). 3-Nitrobenzene boronic acid (1.4 g), $Na_2CO_3$ (2M, 9.2 mL) and tetrakistriphenylphosphine palladium (0.23 g) were added successively. The reaction mixture was refluxed for 6 hours and then cooled and concentrated. The resulting residue was partitioned between 75 mL $H_2O$ and 100 mL of ethyl acetate, and extracted with ethyl acetate (2×100 mL). The extracts were then dried over $MgSO_4$, filtered, concentrated and chromatographed on silica gel (20:80 ethyl acetate:hexane) yielding 1.2 g of 6-isopropyl-8-(3-nitrophenyl)quinoline as a slightly impure yellow oil.

The desired product is obtained in its pure form by recrystallization of its hydrochloride salt. The oil was dissolved in 25 mL of 10% methanol:methylene chloride, to which a solution of 1M $HCl/Et_2O$ (100 mL) was added. The solution was stirred for 10 minutes and then concentrated. The resulting white solid was recrystallized from ethyl acetate:ethanol yielding 0.74 g of 6-isopropyl-8-(3-nitrophenyl)quinoline as pale yellow crystals.

Characteristic analytical data are as follows: elem. anal. calc.(found): c 65.75 (65.92), H 5.21 (5.21), and N8.52 (8.67); and $^1H$ NMR (DMSO) δ 1.37 (d, 6H, J=6.9 Hz), 3.2 (m, 1H, J=6.9 Hz), 7.81 (m, 2H), 7.92 (d, 1H, J=1.9 Hz), 8.09 (d, 1H, J=1.9 Hz), 8.11 (m, 1H), 8.43 (m, 1H), 8.53 (m, 1H), 8.7 (dd, 1H, J=1.5 Hz, J=8.3 Hz), 8.9 (dd, 1H, J=4.7 Hz, J=8.3 Hz).

EXAMPLE 8

Preparation of 6-Methyl-8-Bromoquinoline

8A. Formula 5 Where $R^1$ is Methyl and X is Bromo

A slurry of 2-bromo-4-methylaniline (5 g), glycerol (6.7 g), and arsenic pentoxide (3.9 g) was formed and heated to 100° C. for 30 minutes. Concentrated $H_2SO_4$ (4.9 g) was added dropwise and the mixture was heated to 150° C. for two hours. The progress of the reaction was monitored by thin-layer chromatography (9:1 hexane:ethyl acetate). Upon completion, the reaction mixture was worked up by adding a mixture of $H_2O$, basifying with saturated $NaHCO_3$, extracting with ethyl acetate, and drying the organics layer with $MgSO_4$. The desired product was isolated and purified by column chromatography (9:1 hexane:ethyl acetate), yielding 6-methyl-8-bromoquinoline (1.8 g) as a yellow liquid.

Characteristic analytical data are as follows: $^1H$ NMR ($CDCl_3$) δ 2.5 (s, 3H), 7.4 (dd, 1H, J=8.3 Hz, J=4.3 Hz), 7.52 (bs, 1H), 7.9 (d, 1H, J=1.8 Hz), 8.07 (dd, 1H, J=8.3 Hz, J=1.7 Hz), 8.88 (dd, 1H, J=4.3 Hz, J=1.7 Hz).

8B. Formula 5 Where $R^1$ Is Varied

Following the procedures described in Example 8A the following desired compounds of Formula 5 can be obtained from the indicated starting compounds. For example, 2-bromo-4-isopropylaniline and glycerol can be combined to form 6-isopropyl-8-bromoquinoline, 2-bromo-4-methylaniline and glycerol can be combined to form 6-methyl-8-bromoquinoline, 2-bromo-4-benzylaniline and glycerol can be combined to form 6-benzyl-8-bromoquinoline, 2-bromo-4-(4-pyridylmethyl)aniline and glycerol can be combined to form 6-(4-pyridylmethyl)-8-bromoquinoline, 2-bromo-4-ethylaniline and glycerol can be combined to form 6-ethyl-8-bromoquinoline, 2-bromo-4-(3-propenyl)aniline and glycerol can be combined to form 6-(3-propenyl)-8-bromoquinoline, 2-bromo-4-propylaniline and glycerol can be combined to form 6-propyl-8-bromoquinoline, 2-bromo-4-(n-butyl)aniline and glycerol can be combined to form 6-(n-butyl)-8-bromoquinoline, 2-bromo-4-pentylaniline and glycerol can be combined to form 6-pentyl-8-bromoquinoline, 2-bromo-4-hexylaniline and glycerol can be combined to form 6-hexyl-8-bromoquinoline, 2-bromo-4-(3-pyridylmethyl)aniline and glycerol can be combined to form 6-(3-pyridylmethyl)-8-bromoquinoline, 2-bromo-4-(2-pyridylmethyl)aniline and glycerol can be combined to form 6-(2-pyridylmethyl)-8-bromoquinoline, 2-bromo-4-(cyclopentylmethyl)aniline and glycerol can be combined to form 6-(cyclopentylmethyl)-8-bromoquinoline, 2-bromo-4-(cyclopropylmethyl)aniline and glycerol can be combined to form 6-(cyclopropylmethyl)-8-bromoquinoline, 2-bromo-4-(methylthiomethyl)aniline and glycerol can be combined to form 6-(methylthiomethyl)-8-bromoquinoline, and 2-bromo-4-(methylsulfonylmethyl)aniline and glycerol can be combined to form 6-(methylsulfonylmethyl)-8-bromoquinoline.

EXAMPLE 9

Preparation of 6-Methyl-8-(3-Nitrophenyl)quinoline

9A. Formula I Where $R^1$ is Methyl, $R^3$ is Nitro and $R^2$, $R^4$, $R^5$ and $R^6$ are Hydrogen To a mixture of 6-methyl-8-bromoquinoline (1.0 g), 3-nitrobenzene boronic acid (0.63 g), purchased from Lancaster Chemicals, 2M $NaCO_3$ (1.9 mL), methanol (6.5 mL) and benzene 32 mL) was added palladium tetrakis triphenylphosphine (0.47 g) and heated to reflux for 6 hours. The progress of the reaction was monitored by thin-layer chromatography. Upon completion, the reaction mixture was cooled and the solvents removed. Ethyl acetate was added to the residue and the solution was filtered through a pad of $Na_2SO_4$. The solution was concentrated and the desired product was purified and isolated by preparative thin-layer chromatography yielding 6-methyl-8-(3-nitrophenyl)quinoline (983 mg) as a yellow oil. Characteristic analytical data are: elemental analysis [calculate (found)] C: 72.72 (72.63), H: 4.58 (4.32), and N: 10.60 (10.72).

9B. Formula I, Where $R^1$, $R^2$, $R^3$, $R^4$, $R^5$ and $R^6$ Are Varied

The compounds of Formula I that were prepared following the procedures described in Examples 1–5 (i.e., following Reaction Scheme A) can also be prepared by following the procedures described in Examples 6, 7, 8 and 9 (i.e., following Reaction Scheme B). For example, 6-isopropyl-8-bromoquinoline combined with benzene boronic acid can be converted to 6-isopropyl-8-phenylquinoline, 6-isopropyl-8-bromoquinoline combined with 3-nitrobenzene boronic acid can be converted to 6-isopropyl-8-(3-nitrophenyl)quinoline, 6-benzyl-8-bromoquinoline combined with 3-nitrobenzene boronic acid can be converted to 6-benzyl-8-(3-nitrophenyl)quinoline, 6-methyl-8-bromoquinoline combined with 3-chloro-4-fluorobenzene boronic acid can be converted to 6-methyl-8-(3-chloro-4-fluorophenyl)quinoline, 6-isopropyl-8-bromoquinoline combined with 3-chloro-4-fluorobenzene boronic acid can be converted to 6-isopropyl- 8-(3-chloro-4-fluorophenyl)quinoline, 6-benzyl-8-bromoquinoline combined with 3-chloro-4-fluorobenzene boronic acid can be converted to 6-benzyl-8-(3-chloro-4-fluorophenyl)quinoline, 6-(4-pyridylmethyl)-8-bromoquinoline combined with 3-chloro- 4-fluorobenzene boronic acid can be converted to 6-(4-pyridylmethyl)-8-(3-chloro-4-fluorophenyl)quinoline, 6-methyl-8-bromoquinoline combined with 4-chlorobenzene boronic acid can be converted to 6-methyl-8-(4-chlorophenyl)quinoline, 6-isopropyl-8-bromoquinoline combined with 4-chlorobenzene boronic acid can be converted to 6-isopropyl- 8-(4-chlorophenyl)quinoline, and 6-benzyl-8-bromoquinoline combined with 4-chlorobenzene boronic acid can be converted to 6-benzyl-8-(4-chlorophenyl)quinoline.

9C. Formula I, Where $R^1$, $R^2$, $R^3$, $R^4$, $R^5$ and $R^6$ Are Varied

In addition, other desired compounds of Formula I can be prepared by following the procedures described in Example 9A, and using different starting compounds. For example, 6-ethyl-8-bromoquinoline and 3,4 dichlorobenzene boronic acid can be combined to form 6-ethyl-8-(3,4-dichlorophenyl)quinoline, 6-(3-propenyl)-8-bromoquinoline and 3-trifluoromethylbenzene boronic acid can be combined to form 6-(3-propenyl)-8-(3-trifluorophenyl)quinoline, 6-propyl-8-bromoquinoline and 3-nitrobenzene boronic acid can be combined to form 6-propyl-8-(3-nitrophenyl)quinoline, 6-(n-butyl)-8-bromoquinoline and 3-chlorobenzene boronic acid can be combined to form 6-(n-butyl)-8-(3-chlorophenyl)quinoline, 6-pentyl-8-bromoquinoline and 3,4-dichlorobenzene boronic acid can be combined to form 6-pentyl-8-( 3,4-dichlorophenyl)quinoline, 6-hexyl-8-bromoquinoline and 3-nitrobenzene boronic acid can be combined to form 6-hexyl-8-(3-nitrophenyl)quinoline, 6-(3-pyridylmethyl)-8-bromoquinoline and 3-nitrobenzene boronic acid can be combined to form 6-(3-pyridylmethyl)- 8-(3-nitrophenyl)quinoline, 6-(2-pyridylmethyl)-8-bromoquinoline and 3-chlorobenzene boronic acid can be combined to form 6-(2-pyridylmethyl)- 8-(3-chlorophenyl)quinoline, 6-(cyclopentylmethyl)-8-bromoquinoline and 3-chloro-4-fluorobenzene boronic acid can be combined to form 6-(cyclopentylmethyl)-8-(3-chloro-4-fluorophenyl)quinoline, 6-(cyclopropylmethyl)-8-bromoquinoline and benzene boronic acid can be combined to form 6-(cyclopropylmethyl)- 8-phenylquinoline, 6-(methylthiomethyl)-8-bromoquinoline and benzene boronic acid can be combined to form 6-(methylthiomethyl)- 8-phenylquinoline, and 6-(methylsulfonylmethyl)-8-bromoquinoline and 3-nitrobenzene boronic acid can be combined to form 6-(methylsulfonylmethyl)-8-(3-nitrophenyl)quinoline.

EXAMPLE 10

Preparation of 8-(3-Chlorophenyl)-6-Quinolincarbaldehyde

10A. Formula I Where $R^1$ is Bromomethyl 8-(3-Chlorophenyl-6-methylquinoline (prepared following the procedures described in Example 9, Reaction Scheme B) (1.64 g) was combined with 30 mL of carbon tetrachloride and heated to reflux. N-Bromosuccinamide (1.34 g) and 2,2'-azobis( 2-methylpropionitrile) (0.025 g) was added and the reaction mixture was exposed to light from a 250 W for 1 hour. The reaction mixture was then stirred for an additional 2 hours. The progress of the reaction was monitored by thin-layer chromatography (9:1 hexane/ ethyl acetate). Upon completion of the reaction, the reaction mixture was cooled to 0° C. and poured through a 1" pad of $Na_2SO_4$ on a ½" pad on silica gel. The filtrate was concentrated yielding 2.26 g of a yellow oil as a mixture of the monobrominated compound as the major product as well as the dibrominated compound as the minor product. The crude oil (1.84 g) was dissolved in 25 mL of chloroform and added dropwise to a solution of tetra n-butylammonium dichromate (19.4 g) in methylene chloride (30 mL) and refluxed for 4 hours. The reaction mixture was then cooled to room temperature, filtered through silica gel, eluted with ether and concentrated. The residue was chromatographed in hexane-:ethyl acetate (70:30) to obtain 8-(3-chlorophenyl)-6-quinolincarbaldehyde (0.93 g).

Characteristic analytical data are as follows: $^1$H NMR (CDCl$_3$) δ 7.41 (m, 2H) 7.52 (dd, 1H, J=5.2 Hz, J=4.2 Hz), 7.6 (m, 1H), 7.71 (m, 1H), 8.19 (d, 1H, J=1.9 Hz), 8.38 (d, 1H, J=1.9 Hz), 8.4 (dd, 1H, J=5.2 Hz, J=1.8 Hz), 9.6 (dd, 1H, J=4.2 Hz, J=1.8 Hz), 10.22 (s, 1H); and elemental analysis for $C_{16}H_{10}ClNO$, calc(found) C, 71.78 (71.79); H, 3.77 (3.81); N, 5.23 (5.39).

10B. Formula I Where $R^1$ Is Bromomethyl and $R^2$, $R^3$, $R^4$, $R^5$ and $R^6$ Are Varied Following the procedures described in Example 10A the following desired compounds of Formula I where $R^1$ is bromomethyl can be obtained from the indicated starting compounds. For example, 6-methyl-8-(3-nitrophenyl)quinoline can be converted to 8-(3-nitrophenyl)-6-quinolincarbaldehyde, 6-methyl-8-phenylquinoline can be converted to 8-phenyl-6-quinolincarbaldehyde, 6-methyl-8-(3-chlorophenyl)quinoline can be converted to 8-(3-chlorophenyl)-6-quinolincarbaldehyde, 6-methyl-8-(3-trifluoromethylphenyl)quinoline can be converted to 8-(3-trifluoromethylphenyl)-6-quinolincarbaldehyde, 6-methyl-8-(3-chlorophenyl)quinoline can be converted to 8-(3-chlorophenyl)-6-quinolincarbaldehyde, 6-methyl-8-(3-chloro-4-fluoro-phenyl)quinoline can be converted to 8-(3-chloro-4-fluorophenyl)-6-quinolincarbaldehyde,
6-methyl-8-(3,4-dichlorophenyl)quinoline can be converted to 8-(3,4-dichlorophenyl)-6-quinolincarbaldehyde, and
6-methyl-8-(4-chlorophenyl)quinoline can be converted to 8-(4-chlorophenyl)-6-quinolincarbaldehyde.

EXAMPLE 11

Preparation of 8-(3-Chlorophenyl)-6-(1-Hydroxyethyl)quinoline

11A. Formula I Where $R^1$ Is 1-hydroxyethyl 8-(3-Chlorophenyl)-6-quinolincarbaldehyde (0.8 g) was dissolved in 20 mL of tetrahydrofuran and cooled to −78° C. Methyllithium (4.5 mL, 1.4M) in diethyl ether was added dropwise to the solution over 5 minutes, stirred for 20 minutes, poured into 50 mL of saturated ammonium chloride, and stirred for 5 minutes. The solution was extracted with ethyl acetate (2×75 mL). The extracts were combined and dried over $MgSO_4$, and concentrated. The residue was chromatographed on silica gel (30:70 ethyl acetate:hexanes) to obtain 0.72 g of 8-(3-chlorophenyl)-6-(1-hydroxyethyl)quinoline as a yellow oil.

Characteristic analytical data are as follows: $^1H$ NMR ($CDCl_3$) δ 1.6 (d, 3H, J=6.5 Hz), 5.1 (q, 1H, J=6.5 Hz), 7.4 (m, 3H), 7.55 (m, 1H), 7.67 (m, 1H), 7.7 (d, 1H, J=1.9 Hz), 7.8 (d, 1H, J=1.9 Hz), 8.18 (dd, 1H, J=8.3 Hz, J=1.8 Hz), 8.9 (dd, 1H, J=4.2 Hz, J=1.8 Hz).

11B. Formula I Where $R^1$ Is Formyl and $R^2$, $R^3$, $R^4$, $R^5$ and $R^6$ Are Varied Following the procedures described in Example 11A the following desired compounds of Formula I where $R^1$ is formyl can be obtained from the indicated starting compounds. For example, 8-(3-nitrophenyl)-6-quinolincarbaldehyde and methyllithium can be converted to 8-(3-nitrophenyl)- 6-(1-hydroxyethyl)quinoline, 8-phenyl-6-quinolincarbaldehyde and n-butyl magnesium chloride can be converted to 8-phenyl-6-(1-hydroxypentyl)quinoline, 8-(3-chlorophenyl)-6-quinolincarbaldehyde and ethyllithium can be converted to 8-(3-chlorophenyl)- 6-(1-hydroxypropyl)quinoline, 8-(3-trifluoromethylphenyl)-6-quinolincarbaldehyde and hexyl magnesium chloride can be converted to 8-(3-trifluoromethylphenyl)- 6-(1-hydroxyheptyl)quinoline, 8-(3-chlorophenyl)-6-quinolincarbaldehyde and methyl magnesium chloride can be converted to 8-(3-chlorophenyl)- 6-(1-hydroxyethyl)quinoline, 8-(3-chloro-4-fluorophenyl)-6-quinolincarbaldehyde and methyllithium can be converted to 8-(3-chloro-4-fluorophenyl)- 6-(1-hydroxyethyl)quinoline, 8-(3,4-dichlorophenyl)-6-quinolincarbaldehyde and propyllithium can be converted to 8-(3,4-dichlorophenyl)- 6-(1-hydroxybutyl)quinoline, and 8-(4-chlorophenyl)-6-quinolincarbaldehyde and hexyllithium can be converted to 8-(4-chlorophenyl)- 6-(1-hydroxyheptyl)quinoline.

EXAMPLE 12

Preparation of 6-(4-Pyridyl-N-Oxide-Methyl)-8-(3-Nitrophenyl)quinoline

To a solution of 6-(4-pyridylmethyl)-8-(3-nitrophenyl)quinoline (100 mg) in methylene chloride (10 mL) under nitrogen at room temperature was added m-chloroperoxybenzoic acid (59 mg). The reaction mixture was stirred at room temperature for 3½ hours (the progress of the reaction was monitored by thin-layer chromatography). Upon completion of the reaction, the reaction mixture was worked up by preparation thin-layer chromatography yielding 6-(4-pyridyl-N-oxide-methyl)-8-(3-nitrophenyl)quinoline (87 mg) as creme colored crystals.

Characteristic analytical data are as follows: $^1H$ ($CDCl_3$) δ 4.21 (s, 2H), 7.13 (d, 2H, J=5.2 Hz), 7.43 (dd, 1H, J=8.2 Hz, J=4.2 Hz), 7.5 (d, 1H, J= 1.9 Hz), 7.6 (dd, 1H, J=8 Hz, J=8 Hz), 7.7 (d, 1H, J=1.9 Hz), 7.95 (ddd, 1H J=7.7 Hz, J=1.4 Hz, J=1.3 Hz), 8.13 (d, 2H, J=5.2 Hz), 8.18 (dd, 1H, J=8.2 Hz, J=1.7 Hz), 8.21 (ddd, 1H, J=8.2 Hz, J=J.14, J=1.3 Hz), 8.55 (dd, 1H, J=1.3 Hz, J=1.3 Hz), 8.92 (dd, 1H, J=4.2 Hz, J=1.7 Hz).

EXAMPLE 13

Determination of Potency and Selectivity of Inhibitors for PDE IV

Preparation of Human Platelet Phosphodiesterase (PDE III)

Platelet high-affinity cAMP PDE (PDE III) was obtained from human blood in accordance with previously described procedures described in Mol. Pharmacol. 20:302–309, Alvarez, R., Taylor, A., Fazarri, J. J., and Jacobs, J. R. (1981).

Blood was collected into evacuated tubes containing EDTA (7.7 mM, final concentration). PRP was obtained by centrifuging the blood in polycarbonate tubes at 200× g for 15 min at 4° C. A platelet pellet was resuspended in a volume of buffer A (0.137M NaCl, 12.3 mM Tris-HCl buffer, pH 7.7, containing 1 mM $MgCl_2$. The hypotonically-lysed platelet suspension was centrifuged at 48,000× g for 15 min and the supernatant was saved. The pellets were frozen on dry ice and briefly thawed at 22° C. The supernatant was combined with the pellet fraction and the resulting suspension was centrifuged at 48,000× g for 30 min. The supernatant fraction was stored in 0.5 mL aliquots at −20° C. and used as the soluble PDE. Enzyme activity was adjusted to 10–20% hydrolysis after 10 minutes of incubation by dilution with 10 mM cold Tris-HCl buffer, pH7.7.

Preparation of Human Lymphocyte Phosphodiesterase (PDE IV)

Human B cell line (43D) were cultured at 37° C. in 7% $CO_2$ in RPMI 1640 with L-glutamine and 10% Nu-Serum. Prior to the assay ~1.5×10⁸ cells were centrifuged at 1000 rpm for 10 minutes in a table top clinical centrifuge. The pellet was resuspended in 2–3 mL of 45 mM Tris-HCl buffer, pH 7.4. The suspension was homogenized and centrifuged at 12,000× g 4° C. for 10 minutes. The supernatant was diluted to 28 mL with Tris-HCl buffer and used directly in the assay or stored at −20° C. The final concentration of DMSO in the PDE incubation medium was 1%. Nitraquazone was included in each assay (10 and 100 μM) as a reference standard.

Human Platelet cAMP Phosphodiesterase Assay

The phosphodiesterase incubation medium contained 10 mM Tris-HCl buffer, pH 7.7, 10 mM $MgSO_4$, 0.1–1 μM [$^3$H]-AMP (0.2 μCi) in a total volume of 1.0 mL. Following addition of the enzyme, the contents were mixed and incubated for 10 min at 30° C. The reaction was terminated by immersing the tubes in a boiling-water bath for 90 sec. After the tubes were cooled in an ice-water bath, 0.1 mL (100 μg) of 5'-nucleotidase from snake venom (Crotalus atrox, Sigma V-7000) was added to each tube. The contents were mixed and incubated for 30 min at 30° C. The nucleotidase reaction was terminated by immersing the tubes in a boiling water bath for 60 sec. Labeled adenosine was isolated from alumina columns according to the method described in Anal. Biochem., 52:505–516 (1973), Filburn, C. R., and Karn, J. Assays were performed in triplicate. Hydrolysis of cAMP ranged from 10–20%. Test compounds were dissolved in DMSO. The final concentration of DMSO in the phosphodiesterase assay was 1% when tested with compounds up to 0.1 mM. When tested at 1 mM the DMSO concentration was 10% and this activity was compared to control PDE activity in the presence of 10% DMSO.

Human Lymphocyte cAMP Phosphodiesterase Assay

The phosphodiesterase incubation medium contained 40 mM Tris-HCl buffer, pH 7.7, 0.1 mM $MgSO_4$, 3.75 mM mercaptoethanol, and 0.1–1.0 µM [$^3$H] cAMP (0.2 µCi) in a total volume of 1.0 mL. The reaction was performed and processed according to the procedure used (above) for human platelet PDE. The final concentration of DMSO was 1%.

The representative compounds of the present invention exhibit potency and selectivity as inhibitors of PDE IV when tested by the human platelet cAMP phosphodiesterase assay and the human lymphocyte cAMP phosphodiesterase assay.

EXAMPLE 14

Determination of Immunosuppressive Activity Utilizing Responses of Human Peripheral Blood Lymphocytes to Mitogen This procedure is a modification of a procedure initially described by Greaves, et al. ["Activation of human T and B lymphocytes by polyclonal mitogens," Nature, 248, 698–701 (1974)].

Human mononuclear cells (PBL) were separated from heparinized whole blood by density gradient centrifugation in Ficoll-Paque (Pharmacia). After washing, $5\times10^4$ cells/well are cultured in microtiter plates with minimal essential media supplemented with 1% human serum, gentamicin, sodium bicarbonate, 2-mercaptoethanol, glutamine, non-essential amino acids, and sodium pyruvate. The mitogen concanavalin A (Sigma) is used at a concentration of 2 µg/ml. Test materials are tested at concentrations between $10^{-4}$ and $10^{-10}$M, by addition to the culture at time 0. Cultures are set up in quadruplicate and incubated at 37° C. in a humidified atmosphere with 5% $CO_2$ for 48 hours. A pulse of 1.0 µCi/well of $^3$H-thymidine is added for the last 4 hours. Cells are collected on glass fiber filters with an automatic harvester and radioactivity is measured by standard scintillation procedures. The 50% inhibitory concentration ("$IC_{50}$") for mitogenic stimulation is determined graphically.

The representative compounds of the present invention showed immunosuppressive activity when tested by this method.

EXAMPLE 15

Determination of Immunosuppressive Activity Utilizing The Hemolytic Plaque Forming Cell Assay This procedure is a modification of "The agar plaque technique for recognizing antibody producing cells," a procedure initially described by Jerne, et al. [Cell-bound Antibodies, Amos and Kaprowski editors (Wistar Institute Press, Philadelphia, 1963) p. 109].

Groups of 5–6 adult C3H female mice were sensitized with $1.25\times10^8$ sheep red blood cells (SRBC) and simultaneously treated with an oral dosage form of the test material in an aqueous vehicle. Animals in a control group receive the same volume of vehicle. Four days after SRBC inoculation, spleens are dispersed in glass homogenizers. The number of nucleated cells (WBC) is determined and the spleen cell suspension is mixed with SRBC, guinea pig complement and agar solution at 0.5% concentration. Aliquots of the above mixture (0.1 mL) are dropped on four separate quadrants of a Petri dish and are covered with cover slips. After two hours incubation at 37° C., areas of hemolysis around plaque-forming cells (PFC) are counted with a dissecting microscope. Total WBC/spleen, PFC/spleen and PFC/$10^6$ WBC (PPM) are calculated for each mouse spleen. Geometric means of each treatment group are then compared with the vehicle-treated control group.

The representative compounds of the present invention showed immunosuppressive activity when tested by this method.

EXAMPLE 16

Determination of Anti-Inflammatory Activity Utilizing Arachidonic Acid-Induced Ear Edema in the Mouse This procedure is a modification of a procedure described by Young et al., J. Invest. Derm., 82:367–371 (1984).

Female Charles River ICR mice 23–27 grams are administered 0.2 mL of test material. The mice are later challenged with 20 µl of arachidonic acid applied topically to the ear. One hour after challenge, the weight of an 8 mm disc is determined. The mean increase in ear plug weight is calculated. Materials with anti-inflammatory activity inhibit the increase in ear plug weight.

The representative compounds of the present invention exhibited anti-inflammatory activity when tested by this method.

EXAMPLE 17

Determination of Anti-Inflammatory Activity Utilizing Adjuvant-Induced Arthritis In The Rat This procedure is a modification of a procedure initially described by Pearson, C. M., Proc. Soc. Exp. Biol. Med., 91:95–101 (1956).

Female Charles River albino rats weighing 160–180 g receive 0.1 mL of a suspension in paraffin oil of heat-killed *Mycobacterium butyricum* (10 mg/ml) by means of an intradermal injection into the proximal ¼ of the tail on day 0. Beginning on day 1, the test material is administered orally in an aqueous vehicle (0.5 mL/dose) once each day for 17 days. On day 18 the intensity of the swelling of the four foot pads and tail is determined utilizing a scoring system in which the swelling in the four paws was scored 0–4 for each paw and the tail swelling is scored 0–3, such that the total maximum score is 19.

The representative compounds of the present invention exhibited anti-inflammatory activity when tested by this method.

EXAMPLE 18

Determination of Activity Towards Autoimmune Disease Utilizing Survival of MRL/lpr Mice MRL/lpr mice develop a multisystemic disease characterized by glomerulonephritis, arthritis, arteritis, lymphoid hyperplasia. The length of survival of mice with this disease is approximately one-third that of non-disease developing MRL/n mice. These mice have a high incidence of autoantibodies and the disease process is considered autoimmune in nature as described by Theofilopoulos, et al., Advances in Immunology, 37:269–390 (1985).

The representative compounds of the present invention significantly extended the lifespan of the MRL/lpr mice.

EXAMPLE 19

Determination of Analgetic Activity Utilizing Phenylquinone-Induced Stretching in the Mouse This procedure is a modification of a procedure described by Hendershoot, et al. J. Pharmacol. Exp. Ther., 125:237–240 (1959).

Groups of 8 Female CD-1 mice are administered test materials orally in an aqueous vehicle. At various times following administration of test materials, 0.25 mL of a 0.02% solution of phenylquinone is administered intraperitoneally. The number of stretches for each animal is enumerated over a ten minute period following the phenylquinone administration. Analgetic activity is determined by inhibition of the mean number of stretches.

The representative compounds of the present invention showed analgetic activity when tested by this method.

EXAMPLE 20

Capsule Formulation

This example illustrates the preparation of a representative pharmaceutical formulation for oral administration containing an active compound of Formula I, e.g., 6-isopropyl-8-(3-nitrophenyl)quinoline.

| Ingredients | Quantity (mg/capsule) |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1–12 can be used as the active compound in the preparation of the orally administrable formulations of this example.

EXAMPLE 21

Oral Formulation

This example illustrates the preparation of a representative pharmaceutical formulation containing an active compound of Formula I, e.g., 6-isopropyl-8-(3-nitrophenyl)quinoline.

An suspension for oral administration is prepared having the following composition:

| Ingredients | Quantity |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Examples 1–12 can be used as the active compound in the preparation of the orally administrable formulations of this example.

EXAMPLE 22

Tablet Formulation

This example illustrates the preparation of a representative pharmaceutical formulation containing an active compound of Formula I, e.g., 6-isopropyl-8-(3-nitrophenyl)quinoline.

A tablet for oral administration is prepared having the following composition:

| Ingredients | Quantity (mg/tablet) |
| --- | --- |
| Active compound | 400 |
| corn starch | 50 |
| lactose | 145 |
| magnesium stearate | 5 |

The above ingredients are mixed intimately and pressed into single scored tablets.

Other compounds of Formula I, such as those prepared in accordance with Examples 1–12 can be used as the active compound in the preparation of the tablet formulations of this example.

EXAMPLE 23

Injectable Formulation

This example illustrates the preparation of a representative pharmaceutical formulation containing an active compound of Formula I, e.g., 6-isopropyl-8-(3-nitrophenyl)quinoline.

An injectable preparation is prepared having the following composition:

| Ingredients | Quantity |
| --- | --- |
| Active compound | 0.2 g |
| water (distilled, sterile) | q.s to 20.0 mL |

Other compounds of Formula I, such as those prepared in accordance with Examples 1–12 can be used as the active compound in the preparation of the injection administrable formulations of this example.

EXAMPLE 24

Suppository Formulation

This example illustrates the preparation of a representative pharmaceutical formulation containing an active compound of Formula I, e.g., 6-isopropyl-8-(3-nitrophenyl)quinoline.

A suppository totalling 2.5 grams is prepared having the following composition:

| Ingredients | Quantity |
| --- | --- |
| Active compound | 500 mg |
| witepsol H-15* | q.s to 2.5 g |

(*triglycerides of saturated vegatable fatty acid; a product of Riches-Nelson, Inc., New York, N.Y.).

Other compounds of Formula I, such as those prepared in accordance with Examples 1–12 can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula

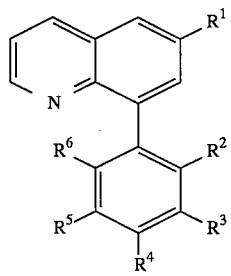

Formula I wherein:

$R^1$ is independently selected from lower-alkyl, cycloalkyl, cycloalkyl lower-alkyl, lower-alkoxy, (lower-alkyl)hydroxylmethyl, aryl, arylmethyl, pyridylmethyl, where aryl, arylmethyl and pyridylmethyl are unsubstituted or independently mono, di or tri substituted with hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl; and $R^2$, $R^3$, $R^4$, $R^5$ and $R^6$ are independently selected from hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl, provided that when $R^1$ is methoxy, $R^4$ is not amino or nitro;

or a pharmaceutically acceptable ester, ether, N-oxide or salt thereof.

2. The compound of claim 1 wherein $R^1$ is a pyridylmethyl group.

3. The compound of claim 2 wherein $R^1$ is 4-pyridylmethyl.

4. The compound of claim 1 wherein $R^1$ is a lower alkyl group.

5. The compound of claim 4 wherein $R^1$ is isopropyl.

6. The compound of claim 1 wherein $R^3$ is selected from the group consisting of chloro, bromo, fluoro, iodo, nitro, hydroxycarbonyl, lower-alkoxycarbonyl, trifluoromethyl and cyano.

7. The compound of claim 6 wherein $R^3$ is nitro.

8. The compound of claim 6 wherein $R^3$ is chloro.

9. The compound of claim 1 wherein $R^3$ and $R^4$ are selected from the group consisting of chloro, bromo, fluoro, iodo, nitro, hydroxycarbonyl, lower-alkoxycarbonyl, trifluoromethyl and cyano.

10. The compound of claim 9 wherein $R^3$ is chloro and $R^4$ is fluoro.

11. The compound of claim 1 wherein $R^2$, $R^4$, $R^5$ and $R^6$ are hydrogen.

12. The compound of claim 1 wherein $R^1$ is isopropyl, $R^3$ is selected from the group consisting of chloro, bromo, fluoro, iodo, nitro, hydroxycarbonyl, lower-alkoxycarbonyl, trifluoromethyl and cyano, and $R^2$, $R^4$, $R^5$ and $R^6$ are hydrogen.

13. The compound of claim 12 wherein $R^3$ is nitro.

14. The compound of claim 1 wherein $R^1$ is 4-pyridylmethyl, $R^3$ is selected from the group consisting of chloro, bromo, fluoro, iodo, nitro, hydroxycarbonyl, lower-alkoxycarbonyl, trifluoromethyl and cyano, and $R^2$, $R^4$, $R^5$ and $R^6$ are hydrogen.

15. The compound of claim 14 wherein $R^3$ is nitro.

16. The compound of claim 1 wherein $R^1$ is 4-pyridylmethyl, $R^3$ and $R^4$ are selected from the group consisting of chloro, bromo, fluoro, iodo, nitro, hydroxycarbonyl, lower-alkoxycarbonyl, trifluoromethyl and cyano, and $R^2$, $R^5$ and $R^6$ are hydrogen.

17. The compound of claim 16 wherein $R^3$ is chloro and $R^4$ is fluoro.

18. The compound of claim 1 wherein $R^1$ is methyl, $R^3$ is selected from the group consisting of chloro, bromo, fluoro, iodo, nitro, hydroxycarbonyl, lower-alkoxycarbonyl, trifluoromethyl and cyano, and $R^2$, $R^4$, $R^5$ and $R^6$ are hydrogen.

19. The compound of claim 18 wherein $R^3$ is nitro.

20. A pharmaceutical composition comprising a pharmaceutically acceptable excipient and a therapeutically effective amount of a compound of the formula

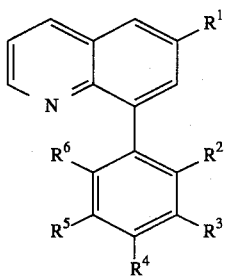

Formula I wherein:
R¹ is independently selected from lower-alkyl, cycloalkyl, cycloalkyl lower-alkyl, lower-alkoxy, (lower-alkyl)hydroxylmethyl, aryl, arylmethyl, pyridylmethyl,
  where aryl, arylmethyl and pyridylmethyl are unsubstituted or independently mono, di or tri substituted with hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl; and R², R³, R⁴, R⁵ and R⁶ are independently selected from hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl, provided that when R¹ is methoxy, R⁴ is not amino or nitro;

or a pharmaceutically acceptable ester, or ether salt thereof.

21. A method of use as an anti-inflammatory agent, immunosuppressive agent, anti-allograft rejection agent, anti-graft-vs-host disease agent, anti-allergic agent, anti-asthma agent, anti-rhinitis agent, anti-atopic dermatitis agent, bronchiodilation agent, anti-autoimmune disease agent or analgetic agent, by administering to a mammal in need of such treatment a therapeutically effective amount of a compound of the formula

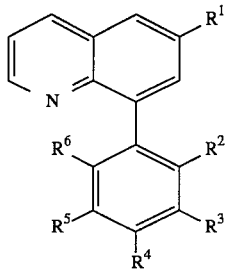

Formula I wherein:
R¹ is independently selected from lower-alkyl, cycloalkyl, cycloalkyl lower-alkyl, lower-alkoxy, (lower-alkyl)hydroxylmethyl, aryl, arylmethyl, pyridylmethyl,
  where aryl, arylmethyl and pyridylmethyl are unsubstituted or independently mono, di or tri substituted with hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl; and R², R³, R⁴, R⁵ and R⁶ are independently selected from hydrogen, hydroxy, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl, provided that when R¹ is methoxy, R⁴ is not amino or nitro;

or a pharmaceutically acceptable ester, ether or salt thereof.

* * * * *